(12) United States Patent
Omura et al.

(10) Patent No.: US 7,670,827 B2
(45) Date of Patent: Mar. 2, 2010

(54) **STRAIN BELONGING TO THE GENUS *STREPTOMYCES* AND BEING CAPABLE OF PRODUCING NEMADICTIN AND PROCESS FOR PRODUCING NEMADICTIN USING THE STRAIN**

(75) Inventors: Satoshi Omura, Tokyo (JP); Haruo Ikeda, Kanagawa (JP); Yumiko Ogasawara, Kanagawa (JP)

(73) Assignee: The Kitasato Institute, Tokyo (JP)

( * ) Notice: Subject to any disclaimer, the term of this patent is extended or adjusted under 35 U.S.C. 154(b) by 598 days.

(21) Appl. No.: 10/535,263

(22) PCT Filed: Jun. 11, 2003

(86) PCT No.: PCT/JP03/07407

§ 371 (c)(1),
(2), (4) Date: Apr. 10, 2006

(87) PCT Pub. No.: WO2004/111230

PCT Pub. Date: Dec. 23, 2004

(65) Prior Publication Data

US 2006/0234353 A1 Oct. 19, 2006

(51) Int. Cl.
C12N 1/21 (2006.01)
(52) U.S. Cl. .................................. 435/252.35; 435/119
(58) Field of Classification Search .................. None
See application file for complete search history.

(56) References Cited

U.S. PATENT DOCUMENTS

| 5,312,753 | A | 5/1994 | MacNeil et al. |
| 5,510,251 | A | 4/1996 | Carter et al. |
| 2005/0003409 | A1* | 1/2005 | Huang et al. ............ 435/6 |

FOREIGN PATENT DOCUMENTS

JP 2003-33188 2/2003

WO WO 93/18779 9/1993

OTHER PUBLICATIONS

Dorchies et al., Veterinary Parasitology, vol. 65, Issues 1-2, Oct. 15, 1996, pp. 163-168.*
Carter et al., J. Antibiot. 1988, vol. 41, No. 4, p. 519-529.*
Nakagawa, K. et al., Microbial Conversion of Milbemycins: Hydroxylation of Milbemycin A4 and Related Compounds by *Cunninghamella echinulata* ATCC 9244. J. Antibiot., 1991, vol. 44, No. 2, pp. 232 to 240.
Haruo Ikeda et al., Combinatorial Biosynthesis-Polyketide Kgobutsu o Rei to shite-, Protein, Nucleic acid and Enzyme, vol. 43, No. 9, (1998), pp. 1265 to 1277.
Haruo Ikeda et al., "Metabolic Engineering no Tenkai-1 Biseibutsu 2ji Taisha Sanbutsu Seigosei no Kinoteki Kakuhen ni yoru Yuyo Bushitsu no Sangyo", Kagaku to Seibutsu, vol. 34, No. 11, (1996), pp. 761 to 771.
Haruo Ikeda et al., "Series Taisha Kogaku/Seigosei Kogaku (4) Seigosei (2) Hosenkin Polyketude Segosei Idenshi no Kaiseki to sono Oyo", Bioscience & industry, vol. 59, No. 8, (2001), pp. 530 to 533.
MacNeil D.J. et al., A Comparison of the Genes Encoding the Polyketide Synthases for Avermectin, Erythromycin, and Nemadectin. Ind. Microorg. (Edited by Baltz R.H. et al.), 1993, pp. 245 to 256.
Shih T.L. et al., Synthesis of an Avermectin-Nemadectin Hybrid. Tetrahedron Lett., 1991, Vo.32, No. 30, pp. 3663 to 3666.
Gibbons P H et al: "Use of an avermectin gene cluster probr to isolate genes involved in nemadectin biostnthesis" Abstracts of the general meeting of the american society for microbiology, vol. 92. 1992, p. 311, XP009069029 & 92$^{ND}$ genreal meeting of the american society for microbiology, new orleans, louisiana, USA, May 26-3.

* cited by examiner

Primary Examiner—Irene Marx
(74) Attorney, Agent, or Firm—Young & Thompson

(57) ABSTRACT

In the present invention, a recombination of gene groups of nemadectin aglycon biosynthesis is performed for obtaining C-13 hydroxylnemadectin, to which sugar groups can be attached, and a production strain which produces C-13 hydroxylnemadectin is produced. Further, C-13 glycosylnemadectin producing strain is prepared by introducing aveBI-BVIII genes involving glycosidation of avermectin and biosynthesis of oleandrose. As described, C-13 hydroxylnemadectin and C-13 glycosidated nemadectin can be obtained effectively by using the producing strain prepared by means of the molecular genetic technology, and improvement in the biological activity thereof can be expected.

1 Claim, 6 Drawing Sheets

SEQUENCE LISTING

<160> NUMBER OF SEQ ID NOS: 6

<210> SEQ ID NO 1
<211> LENGTH: 23
<212> TYPE: DNA
<213> ORGANISM: Streptomyces avermitilis -continued

<400> SEQUENCE: 1
gtgctgcaag gcgattaagt tgg                                                23

<210> SEQ ID NO 2
<211> LENGTH: 22
<212> TYPE: DNA
<213> ORGANISM: Streptomyces avermitilis

<400> SEQUENCE: 2
tccggctcgt atgttgtgtg ga                                                 22

<210> SEQ ID NO 3
<211> LENGTH: 39912
<212> TYPE: DNA
<213> ORGANISM: Streptomyces avermitilis

<400> SEQUENCE: 3
gaattcttcg gcatcagccc ccgcgaagcc ctcgccatgg accccagca acgactcctc         60
ctcgaaaccg cctgggaaac catcgaacac gccggcatca cccccacac cctccacggc        120
accccaccg gagtcttcgc cggaatcaac gctcaagacc acgccgcgca tatccgccaa        180
agccgtgatg tggagaccat cgagggctac gccctgaccg gcagttcggg aagtgtggcg      240
tccggccggg tggcctacac gctcgggctc gaaggccccg cggtgtcggt ggatacggcg      300
tgttcgtcgt cgttggtggc gttgcattgg gcggcgcagg cgttgcgtgc gggtgagtgt      360
tcgatggcgc ttgccggggg tgtgacggtg atgtcgtctc cgggtacgtt tgtggagttc      420
tcacgtcagc ggggtctggc cgcggacggg cggtgcaagg cctattcggc ggctgctgac     480
ggtaccggct gggccgaggg tgtggggatg ctgctggtgg agcggctctc cgacgcccgt      540
cgcaacggtc accgtgtcct ggccgtggtg cgtggcagtg cggtcaacca ggacggtgcg     600
agcaacggtc tgaccgcgcc caacgggccc tcccagcagc gtgtcatccg tcaggccctg     660
gccaatgcgg gactgacccc ggccgatgtc gacgcagtgg agggccacgg caccgggacc      720
actctggggg acccgatcga ggcccaggca ctcctggccg cctacggaca caccgcccc       780
caccaccgcc ccttgtggct gggatccctc aaatccaaca tcgggcacgc acaggccgcc      840
gcgggcgtgg gcggagtcat caagatggtg atggccctgc gcaacgggct gctgccacag     900
accctccacg tggacgagcc cacccccag gtcgactggt ccacaggcgc agtacaactc       960
ctgacacaac cggtgccctg gccgccgac ccggccggcc ggccacgcca cgccggcgtg       1020
tcatcattcg gcgtcagcgg caccaacgcc cacatcatcc tcgaagaagc acccactccc     1080
caggacagcg ataccgacga cgaaccgcct gccaacgcac cagccctgcc ccatcccctc     1140
cctcttcccg tgccggtgtc ggcgaggtct gaggccgggt tgcgggcgca ggcacaggcg     1200
ttgcgccagt acgtggcagc ccgccccgac atgtcacctg ccgacattgg tgcgggtctg     1260
gccccgcggcc gggccgtact ggaacaccgc gccgtcatcc tggccgcgga ccgcgaggaa    1320
ctggcgcagg cactgacagc cctggcagcc ggcgaacccc accccacat caccacaggc      1380
cacacccggg gcggtgaccg cggcggcgtc gtcttcgtct ccccggaca gggcggccag      1440
tgggccggga tgggcctgac cctgctcacc tcctcacccg tgttcgccga acacatcgac     1500
gcatgcgaga aagccctcac ccctgggtg ccctggtccc tgaccgacat cctgcaccgc    1560
gaccccgacg accccgcatg gcaacaagcc gacgtggtcc agcccgtgct cttcagcatc    1620
atggtctccc tcgccgccct gtggcgctcc tacggcatcg aacccgacgc ggtcctcggc     1680

-continued

```
cactcccagg gagaaatcgc cgccgcccac atctgcggcg cactcagcct gaaagacgcc    1740
gccaaaaccg ttgcactgcg cagccgcgca ctggccgcca tacgaggccg gggcgccatg    1800
gcctcactgc ccctgcccgc ccaggacgtg cagcagctca tttccgaacg gtgggaaggg    1860
cagttgtggg tggcagccct caacggcccc cactccacca ccgtctccgg cgacaccaag    1920
gcggtggatg aggtgctggc gcactgcacc gacaccggcc tacgggccaa acgcatcccc    1980
gtcgactacg cctcccactg ccccacgtc caaccctcc acgacgaact cctgcacctg    2040
ctgggagaca tcaccccca gccgtccacc gtgccgttct tctccaccgt ggaaggcacc    2100
tggctggaca ccacaaccct ggacgccgcc tactggtacc gcaacctcca ccagcccgtc    2160
cgcttcagcc acgccatcca gaccctgacc gacgacggac accgcgcctt catcgaaatc    2220
agcccccacc ccaccctcgt ccccgccatc gaagacacca ccgaaaacac caccgaaaac    2280
atcaccgcga ccggcagcct ccgccgcggc gacaacgaca cccaccgctt cctcaccgcc    2340
ctcgcccaca cccacaccac cggcatcggc acacccacca cctggcacca ccactacacc    2400
caaacccacc cccacccaa ccccacacc cacctcgacc tgcccaccta cccttccaa    2460
caccagcact actggctcca accacccacc acaacaaccg acctcaccac caccggcctc    2520
accccacccc accacccct cctcaccgcc acactcaccc tcgccgacaa caacacacaa    2580
ctactcaccg gccgcctctc cctacgcacc caccctggc tcaccgacca caccgtcgcc    2640
ggcatggtcc tcctgccggg caccgcgctc ctcgaactcg ccctccaagc cggcgaacgg    2700
gtggactgcc ctcgggtgga ggaactgacc ctgcacgcac cgttggtgat cccgcacacc    2760
gaggacgtga cgttgcaggt caccgttcgg gcagccgatg agagtggcca tcgcgccctc    2820
gcgatccact cgtactccgg caccgcgtcg tcggcggacc gggagtggac ccgtcacgcc    2880
acgggcctcc tcacacacca cgccgacacc gatcaccgtg ccgacacgca cacggacgcg    2940
tgccttggcg ggagctggcc cccgcccggc gcgcagccca tcgaactggg cgacgtctac    3000
ggtcgtatgg cggcggactc ggacatcgcc tacgggccgg tcttccaggg gctgcacgcc    3060
gcctggaggt tcggcgacga tgtcctggcc gaggtgcgtc tgccggaaga ggctctgcgc    3120
gatgctccgg cggcggcctt cggtgttcac ccggccttgc tcgacgcggc cctgcacgcc    3180
acggcgctca ccccccagaa cggggacggc tcgacggaga acgtcgccca ggagagcatg    3240
cctgaccgcg cagcccacca ggcgcgactg ccgttcagct ggagcggcgt gtccctgcac    3300
acggcgggca gttccgtgtt gcgcgtacgg ctgtcgcgca gtccgcagca cggtaatgcc    3360
gtggccctca ccgcggccga cgaggacggt cggccggtgg tgacgatcga gtcgctcgcg    3420
ctgcggccgg tgtccaccga ggagctgcgc gcggccgcgg atcgtacgcc cgagcacgag    3480
tcgctcttcc gactggactg ggtttccgta ccagtgcccg ccaacgcccc ttcgcccacc    3540
gcggaccggc cctgggcggt catcggcgcg ggccttcccc acctgcccgg cctgacggag    3600
cacgagcacg tgaccgcgta tgacgagccg gcggacctgc ttctggctct ggaccgcggt    3660
gctccgccgc ccggtgtgct ggtcgtaggt ggtgtcgccc acaccgaagc ccgggagtat    3720
tccgccgaag ccccggggga gcgcgggacc gaggcctgcg aggcccggcc ggacgtcgtg    3780
cacgtgggcg tcgtgcacac ggctgccgtg cacgcggctg ccgcgcagat gttggccagg    3840
ctccaggcct ggctgggcga cgagcgcctc gcagacagcc ggctgctcgt cctgacgtgc    3900
ggcgcggtcg cccgcgcctc cggcgacgat gcgacggacc tgcccggggc cgccgtgtgg    3960
gggctggtgc gttcgcgcca gtccgagcac ccggaccgca tcacgctgct ggacttcgag    4020
cggggcacag aggcggagcc cggtcagctg gcgacggcgc tgaactgcgg ggagcggcag    4080
```

```
cttgccgtcc gccccggagg gctgttcacg ccacggctgg tgcgcgcgcc acgtgtcgcc    4140
gacgccgtac ccgccgtacc cgccgtggcc gtaccgtcag cgggtcacgc agccgtaccg    4200
gcagcgggtc ccttccttcc gggcggaacg gtgctgatca ccggcggaac cggtgtcctg    4260
ggccggctcg tggcccggca tctggtggag gcgcacggcg tacggcatct gttgctggcg    4320
ggtcggcgcg gaccggacgc cgagggtgcg ccggagttgc gggcggagct cggtgggctc    4380
ggcgcgacgg tggaggtcgt cgcctgcgac gcggcggacc ggcagcagct ggccgacctg    4440
ctgacacgga tccccgacga tcggccgctg accggtgtcg tgcacagtgc gggcatcctg    4500
gacgacggcg tgatcacgtc gctgtcgccg gagcggctcg gggccgtcct ccgggccaag    4560
gcggacgctg cgctgcttct cgacgagctg acgcgcgggg cagagctgtc ggctttcgtc    4620
atgttctcct ccgcgtcggc ggtggtcggc tcgcccgggc agggcaacta cgccgccgcc    4680
aacgccgtcc tcgacttcct tgctcatcgc cgccgcgccg agggctgcc cgccgtctct    4740
ctcgcctggg gcctgtggga agagggcaca gggatgacgg gccacctcga cgtcgacgac    4800
catgcgcgga tcagccgcgc gggaatgcgc ccgctgccga ctgccgaggc tctggcgctg    4860
ttcgacgcgg ccttggccga cggcgagccg ttcctgatgc cggctcggct cgacctcacg    4920
gccgtacggt ctggtgccgc gtccgcaccg gtgccgccgc tgctgcaagg tctgcttcag    4980
ctgcctcggt cccgctcggc cgccgcgacc cccggccatg gggcccggc ggcggacgag    5040
gcggcggcct ggcgtgagcg tctggcccgg cagagtgccg gtgagcgcag gcaggcgctg    5100
ctgcgcctgg tgcggtcgca tgtcgcgcg gtgctcggcc atagcggtgc cgacggaatc    5160
gacgcatcgc gggcgttccg cgagctgggg ttcgactcgc tcacggcggt cgagctgcgc    5220
aaccgtctca cggccgcgac gggcctgcgg ctgcgggcca cgctggcctt cgatttcccg    5280
accccggcag cgctggccga gcacttgggc gagcgtctgc ttcccgacca ggaggccacg    5340
ggcgagcaag ccgcgatca gctctccggc ggcagcgagg aggacgtacg cagcctcctg    5400
acgtccattc cgatcggcag gctgcgggac gcggggctcc tcgggccccct gctcacgctc    5460
gcggacacgg gccgcggcgc ctcgggcgcc ccgcaggtc cggaggacgc gccgccctcc    5520
ggccaggaca caccggctcc cgtctcgatc gacgagatgg acatcgacga cctgatggat    5580
ctggcgcacg gcatggcac cgcacccgcc cgtgagcccg ccgacgcaga ggactcgtcg    5640
tcatcacgaa accggacaca ccacacacac gaaggtgaga cagcgtgaac ccatccgagc    5700
cgctcggcct gcccaacgaa cgtgtagtag acacccgacc gtccgatgcc acgtctcac    5760
ccgaggccgg cctgaacagg tcaggagcgc tgccccgtga actgctgtcg ttgccggtgg    5820
tggtgtgggc cggggtcggc ctgctgtttc tggccctgca ggcgtacgtg ttcagccgct    5880
gggcggccga cggtggctac cggctgatcg agacggcggg ccagggtcag ggcggcagca    5940
aggatacggg gactaccgat gtggtctatc ccgtgatttc cgtcgtctgc atcaccgccg    6000
cggcggcgtg gctcttccgg aggtgccgtg tcgaacgacg gctgctgttc gacgcccttc    6060
tcttcctcgg gctgctgttc gcgagctggc agagcccgct catgaactgg ttccattccg    6120
ttctcgtctc caacgcgagt gtgtggggcg cggtgggttc ctggggtccg tatgtgcccg    6180
gctggcaggg ggcgggcccg ggtcggagg cggaaatgcc gctggcgtcg gcctccgtct    6240
gcatgtcggc tctgatcgtc accgtgctgt gcagcaaggc actggggtgg atcaaggccc    6300
gccgccggc atggcggacc tggcggctgg tcctggccgt gttcttcatc ggcatcgtgc    6360
tcggtctgtc cgagccgctg ccgtccgcct ccgggatcag cgtatgggcc agagcgctgc    6420
```

-continued

```
ccgaggtgac cttgtggagt ggcgagtggt accagttccc cgtgtatcag gcggtcggtt      6480
ccggcctggt ctgctgcatg ctgggctcgc tgcgcttctt ccgcgacgaa cgcgatgagt      6540
cgtgggtgga acgggagcc tggcggttgc cgcaacgggc agcgaactgg gcgcgtttcc       6600
tcgccgtggt cggtggggtg aatgccgtga tgttcctcta cacctgtttc catatcctcc      6660
tgtccctcgt cggtggacag ccgcccgacc aactgccgga ctccttccaa gcgccggccg      6720
cttactgagt tcagggcagg tcggaggaga cggagaaggg gaggcgaccg gagttccggt      6780
cacctcccct ttgtgcatgg gtggacgggg atcacgctcc catggcggcg ggctcctcca      6840
gacgcaccac actcctcggt tcagcgatca tgcgagtcg gttggggaag acgtgagtgg       6900
ccttcgtctt gggccggacc tcgtcgcccg aagggcgtg tagtcgccag tgggaggcga       6960
cgaccgcgac cgtaacggcc gtctcgagaa gggcgaagtt gtcgccgatg catttgtagg      7020
tgccgagcgc gaagggcacc cacgccccct tgggaactcc gcggctcgat cccttggttt      7080
cccagcggcc ggggtcgaga cgttcgggtt cggggtacca acgtgggtcg cgctggatgg      7140
cgtacgcgct gtacatgacc tccacatcgg cgggcaggtc gtgaccgccg agtcgtacgg      7200
gccgcaccgt ccggcgggac cccacccagc cggggtattt gcgcagtgcc tctttcacga      7260
ggttctgtgt gtacggcagc cgcgggaggt cctcgtgcgt gggcaaccgc cgcccagga      7320 ccgtgtcgag ctctgcgtgc agccgactct cgatctcggc gttctgtccg agtcgtgga      7380 aaatccacgc cgtaatggca gctgggccgc cgatcccggc caccgcgatt cccatgacct      7440
cgtcatggac ctcctggtcc gtcatggagg caccttcggc gtccgtcgcg cgcagcatcg      7500
tcgagagcag gtcaccgtgg tcgcggccat cggcgcgata cgccgtgatc gcctcccgga      7560
tcgttgcgct cgtacggccc acggaccgct tgcccgcggt gggaagaacc tcgtaaaggg      7620
tgggggcgag agcactcagc cgggccacct tcagaatgtc gtgtccggtt ttccgcagcg      7680
ccgcctcggc cttcgcgccc aggtcggaga agaacagcgt cttcgtgatc atggcaagcg      7740
acaggtcgca ggcggcctgc tcaacgtcca ccacctgccc agcgctccag gaatcagcgg      7800
tctcctgcgc ggcggccgcc atggtggcga catagctctc gaggcgctgg cggtggaacc      7860
ctggctgcat ccgcctccgc tgtcgccggt gcgtctcccc cgatacggct acgaggatgg      7920
ggccgatgaa gcggctcgcg ccctgtgcgc ccttgctccg ggtgaaatcg cccgatccgg      7980
aggagaccag catggtccgc accaggtccg ggtgcgtggc gaggtaggcg gttttcggcc      8040
cgaggcggag cttgagcagg tctccgtgat ctgctgcgga gcgaaggaac tccaggggct      8100
gccgcatcaa cggcggcaca tggccgacga ccggccaggc gccgggcgcc tcgggaatgc      8160
tgctcgtcga ctgggacatc acgagtgctc ctttgcgggg tgaagggggg tggctgggag      8220
gggaacgaca gtgacgagtg aagggggagg tgtgggggtt ggcgtcggcc cggggtgag       8280 cgtggacatg ggagtgggag ggagtgaagt gagctcggag tggtttctgg gcttcattga      8340
gattcgaatc cgacttccct gtcgatgaga gcgaacatct cctcgtccga tgtctctgcg      8400
aggtcggggg cggtgtcgtc gccgttcaac ttctgggcga gggaatgcag tcgggaggcc      8460
agccgcgtgc gcgcgccgtc gtccagcggg gcagcggagc atgtggtgga ggagagcact      8520
accgcctcca gccgctcgag ctccgagagc agcgagggca gccccggggg tgtcgttgcg      8580
gcgtccggct cggccgcggc ggtgagtccc ttgctgacga gttgtgtgtg gaggtggtgg      8640
gtgagggtgg tggggttggg gtggtcgaag gcgagggtgg tggggaggcg gagtccggtg      8700
gtgtgggaga gccggttgcg tagttcgacg gcggtgaggg agtcgaagcc gaggtcgcgg      8760
aacgcgcggt cggggggggat ggtgtcgggg gtggtgtggc ccaggacggt ggcgatgtgg      8820
```

```
gagcggacca gggcgaggag ggtggtgtgc tgttgttcgt gtgtctggcc ggccagccgg   8880
ccgtgcagct gggcgccgtt gtccgcacca ccggtagtgg tggtgcgggt ggtgcggcgg   8940
cgggtggcgg gcaggaggtc ctgcagcagg ggcggcaggg gcggggcggg acgcaggtcg   9000
gcgggcagca ggaccggccg gtccagagcc agggccgcat cgaagagggc cagtgcgtcc   9060
ggggtcgaca tgggatgcag accggaacgg atgatgcgcc ggtggtcggt gccggccaga   9120
tgcccggtca tcccgctggc ctcttcccac agccccacg ccagcgacac ccccggcaga    9180
cccgccgccc gccgccggta cgccagcgcg tccagagcgg cattggccgc ggcgtagttg   9240
ccctgcccgg ccgacccag gatccccgcg gccgaggaga acagcacgaa cgccgacagc    9300
tccatacccc gcgtcagctc atccagcaaa agagcggcat ccaccttggc cgcgaacacc   9360
gtgcccagcc gctcgggcgt gagagaggcg atcgtcgcat cgtccagcac accagccgca   9420
tgcacgacac ccgtcagcgg acacccggca ggaacaccct ccagcagccg gaccacctcc   9480
cgccgctccc ccacatcaca cgcaacaatc cgcacctccg cccccaacgc ggccagctcc   9540
gcccgcaaac cctccgcacc cggagcatcc ggaccacgcc ggctcaccaa caacagatcc   9600
cgcaccccac acacaccagc cagatgccgc gccaccgccg cacccagcac accgtccca    9660 cccgtcacca acaccgaccc acccgacaac cacggcaaca cctcccgacc cgatacatca   9720
accggcgact caagtcgtgt caggcgtgcg ggccagcaccc gctcaccacg caccgccaac   9780
tgcggctcac cacacgccac caccgcagcc acacgcccac catccagacc agacccata    9840 ccggcctcgt tgccggcatc gcggtcagcg ccgctgtcga ggtcggtgtc caggtcgagg   9900
aggacaaacc ggtccggatg ctcagcctgc gccgaccgca ccagccccca caccgccgca   9960
cccaccacat ccaccgggcc atccaccggg ccgtcctccg ggccggccac caccgcaccc  10020
cgggtcacca ccaccagccg cgaacccgca aaccgctcca gccccagcca cccctgcacc  10080
acacccaaca ccccaccaac aacctcaccc acaccaccgc caccaccgcc gccatcggca  10140
ccggcatccg ggcaccgcaa caccaccacc cccggcacac catcctcctc agccgccaga  10200
ccaacgaggt cgtcggcacc atccagcacc accaccgatg ccccgcccga caccagtaca  10260
tctgagggca cctcaaccca cttcatgtcg aagagctcag cgcgctgtac ggcgcgctcg  10320
gcagctcgca attcgtccgc cgccaacggg cgcaccgcca acgcctcgac ggacgccacg  10380
ggcgtaccgg tgtcatccgt gaccagcacg gaaactgcgg cgtggccgct gttcggatcg  10440
gccggcgaga gtcgcacgcg caacgacgac gcattggcgg cgtgcagcgt cacaccggtg  10500
aaggagaacg gtacggatcc ctgcggcaga ctgcccgacg gcgcaaaggc cgctgcgtgc  10560
aaggcagcat ccagcagtgc cgggtgcagg ttgtacgcgg atgcctcgcc gtgcacctgt  10620
tctggaaggc gaacctcggc aaacacctcg tctcccagac gccaggcagc agtcagcccc  10680
cggaatgcgg ggccatagac aaagccattt gcctcgtagt cgccatacaa ggctgccaat  10740
tcctcatcag cacagcgaac tgcgcccgct ggcggccaca tcgacagatc atcgtggcta  10800
cggcctgtct caatgcgcga ggtcttggtt cccagaacgg ccgtggcgtg atgacgccag  10860
ggagccgctg cggggggcgtt ctcgcttcgc gagtagatcg tcagtgaacg agtgtcggtg  10920
tcgtccggtg gattgatgtg cacctgaacg tcgacggcac cctcacgggg gatgacgaga  10980
ggcgtgtgga gggcgagttc ttcgaggtgg tcggtcgtgg ttgcttggag ggcgagttcg  11040
aggagggcgg ttcctggcac aagagtggta ccgacgacgg tgtggtcggt gagccagggg  11100
tgggtgcgta gggagaggcg gccggtgagt agttgtgtgt tgttgttggc gagggtgagt  11160
```

```
gttgcggtga ggaggggtg gtgggtgggg gtgaggccgg tggtggtgag gtcggttgtc    11220
gtggtgggtg gttggagcca gtagtgctgg tgttggaagg ggtaggtggg caggtcgagg    11280
tggtggttgt ggggtgggg gtgggtttgg gtgtagtggt ggtgccaggt ggtgggtgtc    11340
cgaatgccgg tggtgtgggt gtgggcgagg gcggtgagga agcggtgggt gtcgttgtcg    11400
ccgcggcgga ggctgccggt cgcggtgatg ttttcggtgg tgttttcggt ggtgtcttcg    11460
atggcgggga cgagggtggg gtgggactg atttcgatga agggcggtg tccgtcgtcg    11520
gtcagggtct ggatggcgtg gctgaagcgg acgggctggt ggaggttgcg gtaccagtag    11580
gcggcgtcca gggttgtggt gtaccagacc aggtgcccta cgacggtgga gaagaacggc    11640
atggtggacg gctggggggt gatgtctccc agcaggtgca ggagttcgtc gtggagggt    11700
tggacgtggg ggcagtggga ggcgtagtcg acggggatgc gtttggcccg taggccggtg    11760
tcggcacagt gggtgaggag ttcttctact gcggtggtgt cgccggagac ggtggtggag    11820
tgggggccgt tgagggctgc cacccacaac tgcccttccc accgttcgga aatgagctgc    11880
tgcacgtcct gggcgggcag gggcagtgag accatggcgc cccggcctcg tacggcggcc    11940
agtgcctggc tgcgcagtgc aacggttttg cggcgtctt tcaggctgag tgcgccgcag    12000
atgtgggcgg cggcgatttc tccctgggag tggccgagga ccgcgtcggg ttcgatgccg    12060
taggagcgcc acaggcggc gagggagacc atgatgctga agagcacggg ctggaccacg    12120
tcggcttgtt gccatgcggg gtcgtcgggg tcgcggtgca ggatgtcggt cagggaccag    12180
ggcacccagg gggtgagggc tttctcgcat gcgtcgatgt gttcggcgaa acgggtgag    12240
gaggtgagca gggtcaggcc catcccggcc cactggccgc cctgtccggg aagacgaag    12300
acgacgccgc cgcggtcact gccccgggtg tggcctgtgg tgatgtgggg gtggggttcg    12360
ccggctgcca gggctgtcag tgcctgcgcc agttcctcgc ggtccgcggc caggatgacg    12420
gcgcggtgtt ccagtacggc ccggccgcgg gccagacccg caccgatgtc ggcaggtgac    12480
atgtccgggc gggctgccac gtactggcgc aacgcctgtg cctgcgcccg caacccggcc    12540
tcagacctcg ccgacaccgg caccggcacc ggcaccggct cagactcagc caccggaagg    12600
gctggattcg gagcacccac cgacaccca ccaccggcag caccgcccgc cgccgcaggc    12660
gcctcctcca aaatcacatg ggcgttggtg ccgctgacgc cgaatgatga cacgccggcg    12720
tggcgtggcc ggccggccgg gtcggcgggc cagggcaccg gttgtgtcag gagttgtact    12780
gcgcctgtgg accagtcgac ctgggggggtg ggctcgtcca cgtggagggt ctgtggcagc    12840
agcccgttgc gcagggccat caccatcttg atgactccgc ccacgcccgc ggcggcctgt    12900
gcgtgcccga tgttggattt gagggatccc agccacaagg ggcggtggtg ggggcggtgt    12960
tgtccgtagg cggccaggag tgcctgggcc tcgatcgggt cccccagagt ggtcccggtg    13020
ccgtggccct ccactgcgtc gacatcggcc ggggtcagtc ccgcattggc cagggcctga    13080
cggatgacac gctgctggga gggcccgttg ggcgcggtca accgttgct cgcaccgtcc    13140
tggttgaccg cactgccacg caccacggcc aggacacggt gaccgttgcg acgggcgtcg    13200
gagagccgct ccaccagcag catccccaca ccctcggccc agccggtacc gtcagcagcc    13260
gccgaatagg ccttgcaccg cccgtccgcg gccagacccc gctgacgtga aactccaca    13320
aacgtacccg gagacgacat caccgtcaca ccccgcgcaa cgccatcga acactcaccc    13380
gcacgcaacg cctgcgccgc ccaatgcaac gccaccaacg acgacgaaca cgccgtatcg    13440
acggtcacgg ccggacccc aaggccaaag ctgtaggcca cccggccggt cgcgacgctg    13500
cctgcgctgc cgttggcgat gaggccttcg aaaccctcgg ggacatggtg gagacgcgcg    13560
```

```
gcgtagtcgt ggtacatcac cccggcgaag acacccgtac gggagccacg catcgacagc    13620
ggatcgatac ccgcccgctc gaacgcctcc cacgacgtct ccagcaacaa ccgctgctgc    13680
ggatccatcg ccaacgcctc acgcggactg atcccgaaga agtccgcatc gaactccccc    13740
gcctcataca aaaacccgcc ataccgcgcg tacgacgtcc ccgaccggtc agggtccgaa    13800
tcaaacaacc cctccagatc ccaccccccga ccggccggaa attcaccaat cgcatcccca    13860
cccgacgcaa ccagctccca caactcctcc ggcgaacaca ccccacccgg aaaacgacac    13920
gccatcccca caatcgcaat cggctcatcc gcggcaacct gatgaagtgc gacctgcgat    13980
ggcgtctcgc cttccgcgtc gtcgcccatc agctcacgac gtaggtgacg cgccagggtc    14040
gctgcattcg gctggtcgaa gaccagactg gtcggcagtc gcagtcccgt tgcctcaccc    14100
aggcggttac ggagttccac cgctgtcaag gagtcgaagc ctaggtcgcg gaacgccgag    14160
tcaacgggga tcatctccgg cgcgttgtgg ccgaggacgg tggcgatgtg ggagcggacc    14220
agggcgagga gggtggtgtg ctgttgttcg tgtgtctggc cggccagccg ggcatgcagc    14280
tgggcgccgt tgtccgcacc accggtagtg gtggtgcggg tggtgcggcg gcgggtggcg    14340
ggcaggaggt cctgcagcag gggcggcagg ggcggggcgg gacgcaggtc ggcgggcagc    14400
aggaccggcc ggtccagagc cagggccgca tcgaagagag ccagtgcgtc cggggtcgac    14460
atgggatgca gaccggaacg gatgatgcgc cggtggtcgg tgccggccag gtgcccggtc    14520
atcccgctgg cctcttccca cagccccccac gccagcgaca cccccggcag acccgccgcc    14580
cgccgccggt acgccagcgc gtccagagcg gcattggccg cggcgtagtt gccctgcccg    14640
gccgacccca ggatccccgc ggccgaggag aacagcacga acgccgacag ctccataccc    14700
cgcgtcagct catccagcaa aagagcggca tccaccttgg ccgcgaacac cgtgcccagc    14760
cgctcgggcg tgagagaggc gatcgtcgca tcgtccagca caccagccgc atgcacgaca    14820
cccgtcagcg gacacccggc aggaacaccc tccagcagcc ggaccacctc ccgccgctcc    14880
cccacatcac acgcaacaat ccgcacctcc gccccaacg cggccagctc cgcccgcaaa    14940
ccctccgcac ccggagcatc cggaccacgc cggctcacca caacagatc ccgcacccca    15000 cacacaccag ccagatgccg cgccaccgcc gcacccagca cacccgtccc acccgtcacc    15060
aacaccgacc cacccgacaa ccacggcaac acctcccgac ccgatacatc aaccggcgac    15120
tcaagtcgtg tcaggcgtgc ggccagcacc cgctcaccac gcaccgccaa ctgcggctca    15180
ccacacgcca ccaccgcagc cacacgccca ccatccagac cagacccccat accggcctcg    15240 ttgccggcat cggcgtcagc gccgctgtcg aggtcggtgt ccaggtcgag gaggacaaac    15300
cggtccggat gctcagcctg cgccgaccgc accagccccc acaccgccgc acccaccaca    15360
tccaccgggc cgtcctccgg gccggccacc accgcacccc gggtcaccac caccagccgc    15420
gaacccgcaa accgctccag ccccagccac ccctgcacca cacccaacac cccaccaaca    15480
acctcaccca caccaccgcc accgccgcca tcggcaccgg catccgggca ccgcaacacc    15540 accaccccccg gcacaggccc accaccgctc tcacccacgt cctcgtgcca cgcccacgcc    15600
tgcccacaca ccggcacagg acccacctca gcccactgca ccgcatacag cgaaccccgc    15660
cgccccgccg aaaccgagac agcacgcaac tgacccatat ccacaggccg caactcaaga    15720
cgatcgaccg acgccaccgg caccccggtg tcgtcggtga tgcgcacgca cacggccgcc    15780
cctgtcgctc caagcgtcga caggcacgcg cgcacggaga ctgcaccatg cgtacggaac    15840
cgcagaccgt tccacacatg gggcacgacg ggcgtccccg gacccgccac agaaagcagg    15900
```

```
ccggtgccct gaagggcagc gtcgagcagg gccgggtgca gaccgtacgc cgccgcgtct    15960
cccgacactt cttcgggaag acgtgcctcg acgaggatgt cgtcgccgta gcgccaggcc    16020
gcgcgcaacc cttggaatgc caggccataa gcaaagccgg cgtcggccat ttgatcgtaa    16080
gccgtgttca ggtcgacagg cgtagctcca acgggaggcc agggtcccgc aagcagctcg    16140
tacgaggcag tgtcatcgtc cttggcaggg ctcagcacac ccgcggcatg acgcgtccac    16200
gcactggccg acgcatcggc tccaccactg ccgccctcac cgcgtgagtg gatggtcatc    16260
atgcggcgac ccgactcgtc cggcgccgca atgcaacct gaagggtcac gtctccgacc    16320
tcaggaatga ccaacggtgt gtggagcgtc agctcgtcca cgtggtcgca acccacactt    16380
tctccggcat gaagggccag ttccgcgaag gccgtacccg gcagcagcac gacaccgcct    16440
accgcatggc cggcgagcca gggatgcgtg cgcaacgaga ggcgcccgt cagtaggcag    16500 ccgtccctt cggccagttc caatgtggcg ccgagtaggg ggtgttcggt ggggtcgagt    16560
ccggctgctg acacgttgcc ggcaccgggc tgtgtgcttt cgagccagta gtggtggtgt    16620 tggaagggt aggtggggag gtcgaggtgg gtgtgggtgt ggggttggtt tggtggtgg    16680 gtgtagtggt ggggggtgcca ggtggtggtg gttttggcga ggttggtgag gaggtgggtt    16740
tgggggtggt ggtgggggtg ggtgagggtg agggtggtgg tgggggtgtt gggaggttg    16800 tggtgggtga gggtggtgag ggtgttgtcg ggtccgagtt cgatgtaggt ggtgacgccg    16860
tgttggtgga gggtttgggt ggtggtggct atgtcgacgg tgttgcgggc ttgttgggtc    16920
cagtagtggg gggtgaggag ttggtcgggt ggggtgttgg cggtgatgag gggggtgtgg    16980
ggtgggtggt aggtgagggt ttgggtgtgc tggtggagtt ggttgaggat ggggttggtg    17040
tggggggagt ggaaggcgtg gttggtgggg agggttttgg ttttgatgcc ttgttgttgg    17100
cagagggtgg tgatgtgttg gacggtgtgg ggggtgccgc tgatgacgag ggaggtgggg    17160
gtgttgatgg cggcgatggc gaggtcgttt tcgtgggcgg tgatgtggtg ggtgatgtgg    17220 tgggggtgg tgtggagggt ggtcatggtg ccggggggca tggtttgcat gagggtggcg    17280
cgttgggtga tgagggtggt ggcgtcggtg agggtgagga tgccggcgag gtgggcggcg    17340
gtgatttcgc cgagggagtg tccggcgtag tagtgggggg tgatgtggta gccgtcggtg    17400
aggaggcggt ggagggcgac ctggaaggcg aagagggcgg gctgggcgta cggggtctgc    17460
tggagcagtg cggccgcttc ttcgagggtg gtggtgtcct gggtgttggg gtcctgggtg    17520 aggagggga ggagggggtg gtcgaggtgg gggtcgaggt gggtgcagat gtcgttgagt    17580
gcggcggcga agacggggtg ggtgtggtag aggccgtggg ccatgccggg gcgttgggtg    17640
ccctgtccgg agcagatgaa tgcggtcttt cctgcggcct ccccggtccc ggtcccgcct    17700
ggggcgctgt tgtggatgac ggcggggtgg ggttcgcctg cggcgagtgc ctggagtgct    17760
tgcaggaagg tgtcgcggtc ggcggcgatg agggtggcgc ggtggtcgaa cacggcgcgg    17820
gcgtgggcga gggtgtatcc gacgtcgcg aggtcgaggc cggggtggtc ggtgaggtgg    17880
gcgtgcaggg cctgggcctg ggcgcgcagg gccggctgcg acttggccga caccagccac    17940
ggccacaccc ctggactgcc ggcagcagcc tcctcgccac taccggcatc ctcgccggcg    18000
ggtggtcccc ccggaacgtc gtcggcgggt gtgtctgacg ggatgttgtg ggcgggtgct    18060
tcttcgagga tgacgtgggc gttggtgccg ctgacgccga atgatgacac tcctgcccgc    18120
cgtagccgcc cctcccccgcc gggccagggc accgtctccg tcagcagctg caccgcaccc    18180
gcggaccagt ccacatgcgg cgacggctca tccacatgca acgtccgcgg cagcagacca    18240
ttccgcagcg ccatcaccat cttgatcacc ccggcgacgc ccgcggcagc ctgtgtgtga    18300
```

-continued

```
ccgacattgg acttgaccga gcccagccac agcggcccct cgccggcacg gtcctgcccg    18360
taggtcgcaa ggagggcctg ggcctcgatc gggtcgccca aagtggtgcc ggtgccgtgg    18420
gcctccaccg catcgacatc accggccgac aagccggcgt tggcgagggc ctggcggatg    18480
acacgctgct gggagggccc gttgggcgcg gtcagcccgt tgctcgcacc gtcctggttg    18540
accgcactgc cacgcaccac ggccaggaca cggtgaccgt tgcgacgggc gtcggagagc    18600
cgctccacca gcagcatccc cacaccctca ccccagccgg tcccgtccgc cgccgccgag    18660
aacgccttgc aatgcccgtc cgcggccaga ccccgctgcc gcgaaaactc cacgaaggca    18720
cccggagacg acatcaccgt cacacccccg gcaagcgcca tcgagcactc acccgcacgc    18780
aacgcctgac aggccagatg taaagccacc aacgacgagg aacaagccgt gtccaccgac    18840
accgcaggac cctcaaaacc aaacgtgtac gagatacgac cggaggccac actcccggat    18900
gtgccggtca ggacatagcc ctcggtgtcg gctgcggcgt tttcgtgcag cctgggtcca    18960
taggcctgcg gaatgaggcc cgcgaacacg cctgtctggc tcccgcgtac ggtcgtaggg    19020
tcaatacctg cctgctccat ggcctcccat gaggcctcca gcagcaatcg ctgctgcggg    19080
tccatcgcca gtgcctcacg cggactgatc ccgaagaagc cggcgtcgaa ctcccccgcg    19140
tcgtagagga aactcccaca gcgggtgtac gaggtgcccg gccgacccgg ttccggatcg    19200
aacagtgctt ccaggtccca cccacggtcc gtcggaaact cgccgaccgt gtccctcccc    19260
gatgcgagca gttcccacag ctcctcggct gaggtgacgc ctccgggata gcggcacgcc    19320
atgccaatga tcgcgacggg ctcgtcctgg tctgcaggca cagccgcagc acggggagct    19380
gggatggagg cagtgctgtc cgagcccaga agttgtgtgt ggaggtggtg ggtgagggtg    19440
gtggggttgg ggtggtcgaa ggcgagggtg gtggggaggc ggagtccggt ggtgcgggag    19500
agccggttgc gtagttcgac ggcggtgagg gagtcgaagc cgaggtcgcg gaacgcgcgg    19560
tcgggggga tggtgtcggg ggtggtgtgg ccgaggacgg tggcgatgtg ggagcggacc    19620
agggcgagga gggtggtgtg ctgttgttcg tgtgtctggc cggccagccg ggcatgcagc    19680
tgggcgccgt tgtccgcacc accggtagtg gtggtgcggg tggtgcggcg gcgggtggcg    19740
ggcaggaggt cctgcagcag gggcggcagg ggcggggcgg gacgcaggtc ggcgggcagc    19800
aggaccggcc ggtccagagc cagggccgca tcgaagagag ccagtgcgtc cggggtcgac    19860
atgggatgca gaccggaacg gatgatgcgc cggtggtcgg tgccggccag gtgcccggtc    19920
atcccgctgg cctcttccca cagccccac gccagcgaca cccccggcag acccgccgcc    19980
cgccgccggt acgccagcgc gtccagagcg gcattggccg cggcgtagtt gccctgcccg    20040
gccgacccca ggatccccgc ggccgaggag aacagcacga acgccgacag ctccataccc    20100
cgcgtcagct catccagcaa aagagcggca tccaccttgg ccgcgaacac cgtgcccagc    20160
cgctcgggcg tgagagaggc gatcgtcgca tcgtccagca caccagccgc atgcacgaca    20220
cccgtcagcg gacacccggc aggaacaccc tccagcagcc ggaccacctc ccgccgctcc    20280
cccacatcac acgcaacaat ccgcacctcc gcccccaacg cggccagctc cgcccgcaaa    20340
ccctccgcac ccggagcatc cggaccacgc cggctcacca acagcagatc ccgcaccccca   20400
cacacaccag ccagatgccg cgccaccgcc gcacccagca caccgtcccc acccgtcacc    20460
aacaccgacc cacccgacaa ccacggcaac acctcccgac cagcaacatc accggaccgc    20520
tgagcaggta catcaacgga cgactcaagt cgcgtcaggc gtgcggccag cacccgctca    20580
ccacgcaccg ccaactgcgg ctcaccacac gccaccaccg ccgccacatg cccaccatcc    20640
```

| | |
|---|---|
| acgccccaac cagcaccagc accagcacca gcaccggtgt cgaggtcggt gccggtgtcg | 20700 |
| gtgtcggtgt cgaggtcgag gaggacaaac cggtccggat gctcagcctg cgccgaccgc | 20760 |
| accagccccc acaccgccgc acccaccaca tccaccgggc cgtcttcttg gccggccacc | 20820 |
| accgcacccc gggtcaccac caccagccgc gaacccgcaa accgctccag ccccagccac | 20880 |
| ccctgcacca cacccaacac cccaccaaca acctcaccca caccaccgcc accgccgcca | 20940 |
| ccggcaccgg catccgggca ccgcaacacc accaccccg gcacaggccc accaccgctc | 21000 |
| tcacccacgt cctcgtgcca cgccacgcc tgcccacaca ccggcacagg acccacctca | 21060 |
| gcccactgca ccgcatacag cgaacccgc cgccccgccg aaaccgagac agcacgcaac | 21120 |
| tgacccatat ccacaggccg caactcaaga cgatcgaccg acgccaccgg cacacccgcc | 21180 |
| tcatccccga ccacgaccga caccgcctca cgcccgccgc cccgccctac agcccacaca | 21240 |
| cgcacccgca caccggtcac acccgcccgg tgaagcgaca caccacccca cacagccggc | 21300 |
| acccgaacac cctccccgaa ccccgcccc tccccaaacc ccgtccacc cggaagcaac | 21360 |
| accgacaacg gctggaccac accatccagc aacgccggat gcagcccaaa accagccgca | 21420 |
| tcaccccacg cctcctccgg cagacacacc tcagccagca aatccccccc atcacgccac | 21480 |
| accgcacgca gccccgaaaa caccggcccc aaaacacaac cagccccagc caaacggtca | 21540 |
| cggacaccat cgacatccac cgccaccgca ccccgcggcg ccacacccc cgccagacca | 21600 |
| tccaccacca caccaccacc agcagcagcc tcaaccagca ccccgaggc atgacacgtc | 21660 |
| cacaccccac ccgacgcacc accccacca caagcactcc caccccgcgc atacacactc | 21720 |
| accaaacgcc gcccctcccc atccgcagcc gcaacccaa cctgcacact cacaccccca | 21780 |
| cccacaggaa ccaccagcgg cgcatgcaca gtgagttgct cgattcgggt gcagcccacg | 21840 |
| cgttcgccaa cctggaccgc cagctccacg aacgccgacc ccgacagcag gaccgcaccc | 21900 |
| cccacctcgt aatcgcccag ccacggatgc gagcgcaagg acaggcgacc cgtcagtagg | 21960 |
| cagccgtccg tgtctgcgag ttggactgtt gccgcgagca gagggtgttc ggccggctcc | 22020 |
| aagccagcag cggcgacgtc acctgctccc gtgggagcgt cgagccagta gtgctggcgt | 22080 |
| tggaagggat aagtggggag gtcgaggtgg tggttgtggg ggtgggtgtg gtggtgggtg | 22140 |
| tagtggtggt gccaggtggt gggtgtgccg atgccggtgg tgtgggtgtg ggcgagggcg | 22200 |
| gtgaggaagc ggcgggtgtc gttgtcgccg cggcggaggc tgccgatcgc ggtgacgtct | 22260 |
| tcggcggtgt cttcggtggt gtcttcgatg gcggggacga gggtggggtg ggggctgact | 22320 |
| tcgacgaaga cgcggtgtcc gtcatccgcc agggcctgga cggcatcgct gaaacggaca | 22380 |
| ggctggtgca ggttgcggta ccagtaggcg gcgtccaggg ttgtggtgtc cagccaggtg | 22440 |
| ccctccaccg tggagaagaa cggcacgccg gacggctgcg ggctgatgtc ccccagcagc | 22500 |
| tccagcaact cctcccgcag gggctgcaca tgggggcagt gcgaggcata gtcgaccggg | 22560 |
| atccgccggg cccgcacccc ggtgccggca cagtacgcca gcacctcgtc caccgcctcg | 22620 |
| gcatccccg agacggcggt ggagcggggg ccgttgaccg ccgccaccca caaccgcccc | 22680 |
| gcccaccgct caccaatgag ctgctccacc tcctgggcag gcagcggcac tgaggccatg | 22740 |
| ccgccccggc cccgcacagc ggccagcgcc cggctgcgca gcgcaacagt cttcgccgcg | 22800 |
| tccttcaggc tcagcgcccc acacacatgc gcggccgcga tctcgccctg ggaatggcca | 22860 |
| aggaccgcgt cgggttcgat accgtaggaa cgccacagag cagccaaaga caccatgacg | 22920 |
| ctgaacagca caggctggac cacatcggcc cgctcccaca ccgcatcccc cgcgtcccgg | 22980 |
| cgcaggatgt ccaccacaga ccagtccacc cacggcgcca gagcctcctc gcacgcctgc | 23040 |

```
atccgccggg cgaacaccgg agaggaggcg agcagacgca cacccatccc ggcccactgc   23100
ccaccctgtc cgggaaacac gaagacgaca ccgccccggt caccacccgg cgcatgaccc   23160
gtggtcaccc gccgatccgg ctcaccgcc gccagcgccc caacccttg caccagctcc   23220 tcacggtccg cggccaggac gaccgcacga tgctccagca cagcccgccc acaggccaga   23280
cccgcaccca catcggcaag cgaaacgtcc ggccggactg ccacgtactg acgcaacgcc   23340
tccgcctgcg cccgcaaccc agcctcagac ctagccgaca ccggcacagg aaccggcacc   23400
ggcaccggca ccggcaccga ctcagccacc ggcgcagaca cagccactgg agcggccacc   23460
gactcagcca ccgaaatggc aagacccgga gcaccctcca acaccccacc cccggcaaca   23520 cagcccccg ccgccggcgc ctcctccaaa atcacatgcg cattcgtgcc actgaccccg   23580
aacgacgaca ctcccgcccg ccgcaaccgc cctgccgcgt ccccggcca cggcaccgcc   23640 tccgtcagca gccgcaccgc ccccgcggac cagtccacct gcggcgacgg ctcatccaca   23700
tgcaacgtcc gcggcaacac cccctcccgc aacgccatca ccatcttgat gaccccaccc   23760 acaccgcgg cagcctgcgc atggccgatg ttcgacttca ccgatcccag ccacagcggc   23820
ctgttaccgg cccgctgccc gtacgtggcg agcaacgcct gcgcctcgat cggatcaccc   23880
agcgtcgtgc ccgtcccatg cccctccacc acatccacat ccgccacgga caaccccgcg   23940
ttcgccaacg cctgccggat caccgctcc tgagccggac cattcggcgc cgtcaaccca   24000
ttcgacgcac cgtcctgatt gaccgcactg ccgcgcagca ccgccagcac ccgatgcccc   24060
agccgcaccg catccgacaa ccgctccacc aacagcatcc cgacgccctc gcccatgccg   24120
gtgccgtcgg ctccacccgc gaaggacttg cagcggccgt ccaccgacag tccgcgctgg   24180
cgtgagaact cgacgaagag gtgcggggtc gacatcaccg tcacaccgcc ggccagcgcg   24240
agcgtgcact cacccgaccg cagcgactgg cacgccagat gcagcgccac caacgacgac   24300
gaacatgccg tgtccaccga gacggcaggg ccctcgagac cgagcgtgta ggcgacgcgg   24360
cccgacgcga cggcgccgcc gctaccgttg ccgatgtagc cctcgaatcc ctcggggatg   24420
gtacccaggc gggatccgta gtcgtggtac atcaccccgg cgaagacacc cgtacggag   24480 ccacgcatcg acagcggatc gatacccgcc cgctcgaacg cctcccacga cgtctccagc   24540
aacaaccgct gctgcggatc catcgccaac gcctcacgcg gactgatccc gaagaagtcc   24600
gcatcgaact cccccgcctc atacaaaaac ccgccatacc gcgcgtacga cgtccccgac   24660
cggtcagggt ccgaatcaaa caaccctcc agatcccacc cccgaccggc cggaaattca   24720
ccaatcgcat ccccacccga cgcaaccagc tcccacaact cctccggcga acacacccca   24780
cccgaaaaac gacacgccat ccccacaatc gcaatcggct cgctggacgc ctccatggcg   24840
gctgccagtt gctcattacg tgcccgcagg gtctggttcg ccttcagaga cgccctaagc   24900
gcgtcgacga gcttttcgct ggacgtgtcc atcactgtct cccaaattca agaagtctca   24960
gaaaggcccg tatggccgta aggggaaag cactgatcga tgccggagcc gaccggatac   25020
caccgactgg ccgactggcc gaccggccga ccgggctgtg cccgacccgc cgatcagggc   25080
cgcgatcagg accgcgatca gaggcgcgat cagcgccgca ctgatgcgat ttctgtcagc   25140
cattcgtcga catgccgagc agtcgaatcc gcaaactgtt ccagcatcgt gaagtgattc   25200
ccctggatgt ccagaacggt gtgcggaact ccccacggcg gcgcatctg ttctccgtcc   25260 cggccgcgca ggaagagggc gggtgtggtg atgtccggag gactccagcc ggagaagatg   25320
cggaagtatc cgcccatggc gaccaggcgt gtgtagtcca cgtccacaaa ctgcgtgacg   25380
```

```
cggtcgaaga tttcacttgt cagcgcggac gcgacaggtg cgatgccgtc gtccgggaga    25440
taggcgtcca tggtcaccac cgcttccgga cggacgccta gacgctccag atgactcgtc    25500
accgcgtaga cgaaccatcc gcccgcggaa tgcccggcga gcgcaaaagg cgcgccgtcg    25560
gtgaaccgga cgatcgcgtc ggcgaacatg cgggtcaccg cgccgattcc ggacggcagg    25620
ggttcgccct ccaggaaccc tggcgcagga acgtaccaga cgtctcggtg tccgttcagt    25680
cccgccgcga aacgtgagta ctggtacacg ctcgacacgg cggcgacggt gggcaggcag    25740
atgagggcgg ccgtgtttc gccccgggcg agtgcttcac cttgggcgcg cgcttcaccc    25800
tgggcgagcc ggacgaacgt cggctccggg atgtccgagg ggtccgtgaa ggcgggccgg    25860
aagaaggagg ccgccgagag cagggccatg gactcctcga tgcggcgggt gtcgtgtccg    25920
atccagaaca gggattcgac ggtttcggtg gaggtgccgc ccctggtctg ctgcttctcg    25980
ctccccgtac tgcgctgctg tccggtctcg gcactccctg cgctcccggc cccggctgcc    26040
gcggcggcag gggccggctc gtccggcgtg cccgcctcgg ccgtcaggcg ggtcgcgagg    26100
tgatcggcga gtgccgcggg gctgggctgg tcgaagatga gcgttgccgg gaggcgcagg    26160
ccggtgacgg cgttgatccg gttgcggagt tcgacggcgg tcagcgagtc gaagccgagg    26220
tcgcggaact cggtgtcggc cgggaccaga tcgtccggga gtgcgccgtc cgcggctgtg    26280
acggcgctgg tggggtggcc gaggacgcg cggcatggg tccgtacgag ttccaggagg    26340
agaccggtgc gctgcgcggg gatggtgagt ccggccaggc gctcgcgcag cgtggcgggg    26400
gtgtcggtcg cgatgccgtg gtcggcggac cgccggggccg ggatgcggat cagcccgtgc    26460
aggatgcgcg gcagggcgcc ggccgtggcc tgtgcgtgga gggtggccgc gtcgagccgg    26520
gtggcgagga gcagcccgtc accgaaaggg ccgaggcgat ccgctgtgtc gaggagcgcg    26580
agtccctgtg cgttggacag ggggagcagg ccgccgcggg ccatgcgcgc gaagtcggtg    26640
ccggcgaggt tgcgggtcat gccgtcggcc tcgccccaaa ggcccaggc gagcgaccgg    26700 cccggcagtg cctgggtgtg gcggtgctgc atcagggcgt ccagaaaggc gttcgccgcg    26760
gtgtagttgc cctgtccggg actgccgaag gaggcggcgg ccgaggagaa gacggtgaag    26820
gtggtgaggc cggcgtcgcg ggtcaggtcg tgcaggtgcg cggcgccgaa cgccttcgcg    26880
tgcaggacgg cctccatgcg ctccggagtg agcgaggtga ggatgccgtc gtcgaccaca    26940
ccggccgtgt ggatcacggc tttcagggg tgctgcgcgg gcacttggtc gaggagcgcg    27000
gcgacggccg cccggtcccc gatgtcgcag gccgcgaccg tggcctcggc gccgaggccg    27060
gcgagttcgg cgaccaggtc ggcggcgccg tccgcggccg tgccgcggcg ggtggccagc    27120
agcaggtgcc gtaccccgtg ggccgtggcg agatgacggg cgacgagccg gccgaggacg    27180
ccggtaccgc ccgtgatgag gaccgtggcc tccgggtccc agtcggcgtc ggtggtgctc    27240
ggctgtggct gccggacggg cactcgtgtc atccgcggga tgcggacggc accatttcgc    27300
agggcgatct gcggttcccc ggccagcagg ggaaggcgt tgcgggaggc gtcggtgtcg    27360
tcggtgtcgg ccagcaggaa ccggtcgggg ttctcggtct gcacggagcg gaccagtccc    27420
cagacgcgcg cgtgtgcgag gtcggacacg ggctcgtcgg gggtcgcggt gaccgagccg    27480
tgcgtgagga gggccaggcg gcaggccgcg agccgttcgt cggcgaccca ttcctggagc    27540
agggcgagga cgcgggtggt ggcttgccgg gtggcgtcgg cgagggcggt ggagtcggcc    27600
ggggccgagc cggccggggc ggaatcggtg agggcggaat cggtgagggc ggaatcggtg    27660
ggggcggatg cgccgtccgg ctcgcacgag atgacgacca tgcccggtgc cggggcgccg    27720
gccgccaggg cttctgcgag agccgccggg tccgggtagg cctgccagga ggcgccgttg    27780
```

| | | | | | |
|---|---|---|---|---|---|
| cgctccagga | cggcggccgt | ccgccgggca | ccggggccga | ttagggccca | gtcggctgtc | 27840 |
| cgtgccggtg | tggtggggag | gtgcagcggc | cgccattcga | tgcggaagag | gtggtcgtgg | 27900 |
| tagccggtgc | gcgcggcctg | gagctgctcg | gcggagacgg | gccggaaggc | gagggacccc | 27960 |
| gcggagatga | cgatgcgtcc | cgatgcgtcg | gtggccagca | gtccgaccgc | gtcctcgtcc | 28020 |
| gtgcggacgg | tgagacggac | gtgcagggtg | gaggcgccgg | aggcggcgac | cgtgacgccg | 28080 |
| gtccaggaga | acggcagcca | gccgtgtccg | tcggcggcgg | catcgccctc | gtggcgcaga | 28140 |
| acgaccgggt | gcagtgccgc | gtccagcagg | gccgggtgca | gggcgtaccg | ggcggcgtcg | 28200 |
| gccgcctgtc | cctccgtgct | ctcgggcagg | gtgacgacgg | cgaacacctc | gtccccgcgc | 28260 |
| cgccagacct | cgcgcagccc | ctggaacacc | ggcccgtatc | ccaggccggc | gccggccagc | 28320 |
| tgctcgtacc | agccgtccag | gtccaccggt | gctgcgtcgg | cgggcggcca | cggttcctgt | 28380 |
| gtgtgctcct | ccgcgggccg | ggcggtgccg | gtcaggacgc | cggtggcgtg | gcaggtccac | 28440 |
| tcggtgccgg | tcgccgccgc | ggacgaggac | gacagtccgt | cgtcttcgcg | ggcgtacagg | 28500 |
| gcgaaggtgc | gccgttcggg | ctcctcgggc | gtctggggc | cctggggtgc | ccgacggag | 28560 |
| agttgcagga | tcaccgagcc | ctgttcggga | aggacgagcg | gtgtccgcag | ggtgagttcc | 28620 |
| tcgacggtgc | cgcagtcgac | ctcgtcgcct | gcgcgcacgg | ccagttccag | gatggccgtg | 28680 |
| ccgggcagca | ggacggtacc | gaagatggcg | tggtcggcca | gccacgggtg | tgtgcgcagg | 28740 |
| gagagacggc | cggtgaagag | gagttcctgc | gactcggcca | gtgccaccgc | ggaaccgagc | 28800 |
| aggggatgcc | cggcggtgcc | gagccccgct | gccgacaggt | ccccggggtg | gccggccgag | 28860 |
| gtgtcgaccc | agtagcggtg | gtgatcgaag | gcgtaggtcg | gcaggtcgag | gtggcgggct | 28920 |
| cgatcgcgtt | cgggcagggc | ggcgggccag | ttgaccgccg | ccgctccgtg | cgtatgcagc | 28980 |
| cgggccaagc | cggtgagcag | ggtgccgggt | tccgggctgt | ccggccgtag | gagcgggatg | 29040 |
| agcaggttct | cttgcggggt | gccggtgtcg | tcgtcggcgg | ggtggctgtc | ggcggtggcc | 29100 |
| tctaggcatt | cctcggccag | tgccgacagg | gtcccgtctg | ggcccagttc | catgaaggtg | 29160 |
| cggactccgt | cggtgtgcag | gcggctgatc | gcgtcgccga | agcgcacggt | ccgccgtacc | 29220 |
| tgccggaccc | agtactcggg | gtcgctcagt | tctcccgccg | ccacgatgtc | gccggtgagc | 29280 |
| gtcgacacca | tgggaatggc | tggttcgctg | taggtcagcg | aggccgcgac | ctgctggaac | 29340 |
| tcctccagca | tcgggtccat | cagcggtgag | tggaaggcat | gcccggttcg | caggcgcttg | 29400 |
| actctccgcc | cgcgctcggc | gaaccagtcc | gccatgttcc | ccacctcgtc | ctcggcgccg | 29460 |
| gagaacacca | ccgaggcggg | tccgttcacg | gccgcgaccg | acacccgggc | ttcccggccg | 29520 |
| tcgagcgcct | gtcgcgcctc | ggcttcgctc | gcccgtacgg | cgaccatggc | gccgcctggt | 29580 |
| gcgagctgct | ccatcaggcg | cccgcgggcc | gccaccaggc | ggcaggctgc | tgccagggga | 29640 |
| agcaccccgg | cgacgtgggc | ggccgcgagc | tcgccgatcg | agtgcccggc | cacgaagtcc | 29700 |
| gcgcgcacgc | cgagacgttc | caggtgccgg | aagagcgcga | cctggacggc | gaacagcgcc | 29760 |
| ggctgggcgt | accgcgtacg | gtccagaaca | tccgcggcat | ccgcgacatc | cgcaagatcc | 29820 |
| gcactggcgt | ggatcagcgg | gcgcaggggc | tggtccaggt | gaccgtccag | ttccgccagt | 29880 |
| acctggtcca | gcgcgtccgc | gtaggccggg | tgagccgcat | acagctgacg | gcccattccc | 29940 |
| acgcgttgcg | tgccctgtcc | ggcgaacagc | atggcggtct | ttccgcgccg | gcggcctgag | 30000 |
| tggccgccac | gcgggccgac | cgacccttcg | atcaggccgt | ccgccgaccg | gccctcggcc | 30060 |
| agcgcgtcga | gggcctgaag | gaagccgtcg | cggtcctcgg | ccacgacgac | ggcccggtga | 30120 |

-continued

```
tcgaacacgg accgctgtgc cgccagggcg tgcgccacgt cggccggccg ggcatcggat      30180
gccctggcag cgaactgccg caaccgtcgc gcctggcccc gcagcgctcg ctcggacttg      30240
gcggagagca gccacgggat gggcaggagg gccggcttgt cggacatggc gtcggcgacg      30300
cactccggtt cagccgactt gtcggacacg gcctcggcga cgcactcagc cgacatctcg      30360
gacatggcgt cggcgacgca ctccggttca gccgacatct cggtcacggc gtcagcgacg      30420
cactccggtt cagccgcctc ctcttgcggc tcggtgaggc ccgccggtcc ggtggcgtcg      30480
accacgtggg gcgcctcgac cggcgcctgc tcgacgatga cgtgcgcctc agccggtacc      30540
ggctcactga tgacgtgcgc ctcgaccggc gcctgctcga tgatgacgtg ggcgttggtc      30600
ccgctgactc cgaacgcgga cgcccgcg cgcctgggcc ggccgttctg ctgccacggt        30660
acgggctcgg tgagaagccg gacgccgccg ctcgaccagt cgatgtgggg ggagggttcg      30720
tcgatgtgca ggctggtcgg caacagttcg tggttcaggg ccatgaccat cttgatcaca      30780
ccggccacac ccgcggcagc ctgcgcatgc ccgatgttcg acttcaccga ccccaaccac      30840
accggccgct cccccgaacg accctgcccg tacgtggcga gcaacgcctg cgcctcgatc      30900
ggatcaccca acgtcgtacc cgtcccgtgc ccctccacca catccacatc cgccacggac      30960
aaccccgcac acgccaacgc ctgccgaatc acccgctgct gcgacggacc attcggcgcc      31020
gtcaacccat tcgacgcacc gtcctgattc accgcactcc cccgcaccac cgccaaaacc      31080
cgatgaccac gacgttcagc ctcggacagc cgctccacca acagcacacc cacaccctcg      31140
gcccagccga ccccatcggc ccccgacccg tacgccttgc accggccgtc cggcgacaga      31200
ccccgctgcc gcgagaactc cacaaacgca cccggcgtcg acatcaccgt cacacccccc      31260
gccaacgcca gcgaacactc ccccgacctc aacgcctgac acgccagatg cagcgccacc      31320
aacgacgacg aacacgccgt atccaccgtc accgccggac cctcgaagcc gaaggtgtag      31380
gaaagccgcc cggagacgac gctgttggag acgccggtga gcgcgtaccc ctcgtggtcc      31440
tgggtgccgc ggcgcaggag ctcggcgtag tcctgctgcg agacgccggc gaagacaccg      31500
gtcgtggacc cgtgcagcgt ggcggggtcg atgcccgccc gctccaacgc ctcccaggac      31560
acctccagca tcaaccgctg ctgcggatcc atcgccaacg cctcacgcgg actgatcccg      31620
aaaaaccccg catcgaactc cgccgcaccc tgcaaaaacc caccacaccg cgtgtaggac      31680
gtacccgccc gccccggctc cggatcatag aaagcctcca cgtcccaacc ccggtcgacc      31740
ggaaactccc ccaccgcatc ccgacccgac gcgatcaact cccagaaatc ctccgccgac      31800
tccacacccc ccggaaaacg gcacgccatc cccacaatgg caatcggctc gtcgacatcc      31860
acacgcggtg ccggggcccg aagggcaagg gcaagggcag tgccggtggt cgggcttccg      31920
ccgctcagct gctcgtggat gtgtgccgcg agtgccaccg gcggggatg gtcgaacacc       31980 agggtcctcg ggaagcgcag gcccgtggcg gtgttgaggc ggttgcgtag ttcgacggcg      32040
gtgagggagt cgaaaccgag gtcgcggaag gcgcgctcgg gcaccaccgc atcggcggtg      32100
ccgtgtccaa ggacggccgc ggcatgggta aggaccaggt ccagcacggt ctcggcctgt      32160
gcggcggggt cgagtccggc gaggcagtcg cgcagcatgc cgccgcgcac ggtgtccacc      32220
gcctccgaca actgaccacc ccactgccca gagacccggg aaccccgcgg cgccccctcc      32280
acatccagcc aaaagcgctc tcgctcgaac gcatacgtcg gcagctccac cccgcaacca      32340
ccagcgaccc cgcgaccaac actcccgaac acaccggacc actcaaccgc caccccaccc      32400
acgaacaact cggccacgga catcaggaag cgtcgcaagc cgccttcgcc ccggcgcaga      32460
gatccgacga ccaggctgtc caagtcaccc atctcgtcca gggtttcctg cacaccgacc      32520
```

```
gcgacggccg gatgcgggca cgcctcgatg aagacggtgt ggccggcgcg gaccagcgcc    32580
tgtgtcgcgt cccggaagcg gacgacctgg cgcaggttgc ggtaccagta gtcggcgtcg    32640
agttcggtgc cgtcgatgcg ttcgccggtg acggtggagt agaagggcac gtcgccggtc    32700
ctcgcgcgga tgggggcgag gagttcgagc agccgcccct ggatcgcctc gacctgcggg    32760
gagtgcgacg cccagtcgac catgagcctg cgggccggta cgtcttcgtg tgacagctcc    32820
tccaccaggg cgtcgaccgc ttccggctcc ccggagacca cggccgaacg cgccccgttc    32880
acggcggcga tgaccagacg gtcgccccat gtcgcaagac gcggctccag cttctcgacc    32940
ggcagaccga ccgatgccat cgccccctgc ccggccagtg cggccagcgc ctggctgcgc    33000
agggcggtga cccgggcggc gtcgtcgagg gagagtgcac cggcgacgta ggccgctgcg    33060
atctcgccct gcgagtgccc ggccaccgcg tccgggtgta caccgtacga gcgccagagc    33120
gccgccagcg agaccatcac cgcgaagagg acgggctgga cgacatcgac gcgttgcaga    33180
gggggtgcgt ccggtgcgcc gcgcaggacg tcgaggagag accagtccag gtacggttcg    33240
agggcttggg cgcagtcgga catctgctgg gcgaagaccg gtgaggagcc gaggagttcc    33300
tgcgccatgc cttcccagtg ggtgccctgt cctccgaaca gcatggcgat cttccgtcg    33360 gccgccggtc cggccacacc ctgtaccacc cccgcggtgg gtgccccctc ggccagtgcg    33420
tcgagtgcgt gcaggaactc gtcgcggtcc tcggccacga ccaccgcacg atgctcgaac    33480
accgaccgct ccgacaccaa gcccgcccg accccagccg gactcacccc cacaccatcc    33540 gcaccccccac caaccgccac aaccccacgc aaccgacgcg cctgccccg caacgccaac    33600 tccgaccgcg ccgacaccac ccacggcacc acccccgaac ccgacaccac ccccggaccc    33660
aactcctgca gccggcccgc accccatcc gcgccccgg acgcctcctc caaaatcaca    33720
tgcgcattcg tcccactcac cccgaacgca gacaccccg cacgccgcag ccgaccctcc    33780 accccccggcc actccacctc atccgccaac acacgaaccg acccactcga ccaatccacc    33840
tgcgacgacg gctcatccac atgcaacgtc cgcggcaaca ccccgcccg caacgccatc    33900 accatcttga tcacacccgc cacacccgca gcagcctgcg catgcccgat gttcgacttc    33960 accgaccccca accacaccgg ccgctccccc gaacgaccct gcccataagt ggcgagcaac    34020
gcctgcgcct cgatcggatc acccaacgtc gtaccccgtcc cgtgcccctc caccacatcc    34080
acatccgcca cggacaaccc cgcacacgcc aacgcctgcc gaatcacccg ctgctgcgac    34140
ggaccattcg cgcgccgtcaa cccattcgac gcaccgtcct gattcaccgc actccccgc    34200 accaccgcca aaaccccgatg accacgacgt tcagcctcgg acagccgctc caccaacagc    34260
acacccacac cctcggccca gccgaccccca tcggccccccg accccgtacgc cttgcaccgg    34320 ccgtccggcg acagaccccg ctgccgcgag aactccacaa acgcacccgg cgtcgacatc    34380
accgtcacac cccccgccaa cgccagcgaa cactcccccg acctcaacgc ctgacacgcc    34440
agatgcagcg ccaccaacga cgacgaacac gccgtatcca ccgtcaccgc cggaccctcg    34500
agccccaggg tgtaggcgac gcgtccggat gtgacgctgc tggacaggcc cgtcatggcg    34560
tagccctcga ggtcctcggt ggcccggcgc acagggtcgg cgtagtcctg actgcacatg    34620
ccggcgaaga caccggtcgt ggacccgcgc aacgtggcgg ggtcgatgcc cgcccgctcc    34680
aacgcctccc aggacaccctc cagcatcaac cgctgctgcg gatccatcgc caacgcctca    34740
cgcggactga tccgaaaaaa ccccgcatcg aactccgccg caccctccag gaaaccgccc    34800
cggcgcgtat acgacgaacc cgcccgcccc ggctccggat catagaaagc ctccacgtcc    34860
```

```
caaccccggt cgaccggaaa ctctcccacc gcatcccgac ccgacgcgac cagttcccac   34920
aagtcctccg ccgactccac accccccgga aaacggcacg ccatcccgac aatcgcaatc   34980
ggctcgtcaa cgtcgacacg cgacgccggg accggaggag caatgtcacg ctggccgccc   35040
gcgccctcct ccagctgttc cttgaggtat ccggccagcg cggagggagt gggtagtcg   35100 aagatcagcg tggtgggcag gaggagcccg gtgacggcgt tgaggcggtt gcgcagttcg   35160
acggcgctca cggagacgaa gcccaggtcg cggaaggctc gctcagggcg tacggcggtg   35220
ggggtgctgt gtccgagcac ggtcgccgcg tacgtacgga ccaggtcgag aagcgcacgt   35280
tcctgctcgg cggtgtccat ggccttgagc cgtgcggaga acgagtcggg ggatgcggtg   35340
gcggtgtcga gtccggtggt ttccggggcg aggcgtgctt cggggatgtc gctgatgagg   35400
ggcgagagtc gggagccggg gagggagttg gcggtgaatc ggtcccagtc gatgtcggcg   35460
accgtcacac aggtctcgtc atggtccaac gcctggccca gtgccaccag cgccgtctcc   35520
ggcgtcatcg ccgccagacc ccgacgccgc atctgcccca cggccccctc cgccatcccc   35580
ccaccagccc acggacccca cgccaccgcc aaccccggca ggccctcacc acgccggtgc   35640
cgaacgattg cctccacata cgcgttcgcc gccgcgtaac tccctgtcc cgccggcccg   35700 aacgtcgccg cagccgacga gaacaccacg aaccccgaaa gatccgcccc ccgcgtcaac   35760
tcatgcagat tccaggccgc cagcgccttc gcccgcagca ccccgtgac acgctcggac   35820 gacaacccct ccaacacccc gtcatccaca actcccgcgg catgcaccac cacacccagc   35880
gggcactccg ccggaacggc cgaccgcaac acctccgcca acgcctcacg gtccgccgca   35940
tcacacgcca ccaccgacac ccgcgcgccc aagcccatca agtccgctcg gagttcttcg   36000
actccctggg cgctctcccc gcgtcggctc accagcagca ggtgttcggc gccacgccgg   36060
gccatccacc gggcgacgtg cgcacccaac tcgccggtgc ctccggtgac gagtacggtg   36120
ccgcggggcc gccactcccg ctccgcgacg gcctcctcca acggcgcccg caccaaccgc   36180
cgcacaaacg ccccccgaaga ccgcacggca aactcactct caccccctcc ccccacaccc   36240
gccagcacac ctaccaaccc atcgaccacc cgctcatcca cgagctccgg cacatcaacc   36300
agcccacccc agcggtccgg tgcctccgcc cccaccacac ggcccagccc ccacaccaca   36360
cccgaggccg gccccacac agcatcccgg ccccccaccg acacggcccc gcccgtcaca   36420
caccacagcc gcgcccccac gcccacatca cccagcgcct gcaccaaccc cacagacgcc   36480
actcccgcct gcacgacgcc actccccag cccacaaggg agacgacacc gccgacagcc   36540
tcaccatcga ccgcctcacg caggtggccg gccaacactt ccctgctcac acacccgct   36600 tccacctcca cccgaaccac tcgcgcccca caccgctcca accctccgc caccacatca   36660 accgggcccg cctcgccctc ggacaccacc agccacgcgc ccgacagccc cctacacca   36720 ccgcccgaaa cgggtcgcca cacctcccga tagcgccacc cgtccaccac ttcacgctcg   36780
tgccgtaccc gccccattc ccccaacgcc gacaccaccg cacccagcga cgccccctca   36840 tccacccccaa ggagcgatgc caccaccccc gcatcaccac actcgaccgc ctcccacaac   36900
ggaccacccc acatcccgga aacccccggaa cctcccgcag atccctcctc cacgtccagc   36960
caaaatcgct cccgctcaaa cgcatacgtc ggcagctcca ccccgcatcc atcaccgacc   37020
tcgcgagcag tccctcgaa cacaccgcc cactcaaccg ccgtcccagc cacgaacaac   37080
tccgccaggg cggtcatgac cgaccgtgcc tccggctggt ccggccgcag ggcggggatg   37140
gcgcgggccg gtgcactgag cgagtcctgt gcgagggccg acagcgtgcc gtcggggccg   37200
atttcgaggc aggtggtgac gccctgttcc tgaagccatg agatgccgtc cgcgaaacgg   37260
```

```
accgtgctgc gggcgtgttc gacccagtag tccggggtgc acatggtctc ggcggggagg   37320
ggcgcgccgg tgacgttgga gacgacggga atccgcgggg cgctgaaggt gacctgctcg   37380
gccgcgcggg ggaagtcgcc caacatggcg tccatgtgcg gcgagtggaa ggcgtggctg   37440
gtccgcagcc gccgggtgcg gcggcctcgt gccgcccatt gctgcgcgag gtccaggacc   37500
gcgtcctcgt ccccggagag gacgatcgac cgcggcccgt tcaccgcggc gtgcgcgacc   37560
cgggatgcgt attcgtcggg cagcgggagg atctcgtcct cggacgcctc gatggccacc   37620
atggctccgc cggacgggag cccttgcatc aggcggcctc gtgcgaccac cagtgccacc   37680
gcgtcggcaa ggcagagcat cccggcgaca tgggcggccg ccagttcacc gacggaatgg   37740
ccgaggacgt agtcgggcgt cagacccag gtctccagca gccggaacag cgccacctcg   37800
aaggcgaaca gggcgggctg ggcgaaaccc gtgtcctcga tcagccggcc ttcgggagag   37860
tcctgcggtg cgaagagtac gtcccgcagc ccaggggcac cggggtcggt gcgggcggtg   37920
tcggcctccg cgcagatctc gtcgatggcc tgggcgaaga cggggtacgc ctcgtacagt   37980
tcgcggccca tgcctgcgcg ctgggttccc tgcccggcga agagtacggc gagttcgccc   38040
gaggtggttc gtccctcgac gacgccgggc acggggcggc cgccggccag tgcgtcgagt   38100
gcgtgcagga actcgtcgcg gtcctcggcc acgaccaccg cacgatgctc gaacaccgac   38160
cgctccgaca ccaaagcccg cccgacccca gccggactca ccccacacc atccgcaccc   38220 ccaccaaccg ccacaacccc acgcaaccga cgcgcctgcc cccgcaacgc caactccgac   38280
cgcgccgaca ccacccacgg caccaccccc gaacccgaca ccaccccggg acccaactcc   38340
tgcagccggc ccgcaccccc acccgcgccc cccgacgcct cctccaaaat cacatgcgca   38400
ttcgtcccca tcaccccgaa cgcagacacc cccgcacgcc gcagccgacc ctccaccccc   38460
ggccactcca cctcatccgc caacacacga accgacccac tcgaccaatc cacctgcgac   38520
gacggctcat ccacatgcaa cgtccgcggc aacaccccccg cccgcaacgc catcaccatc   38580
ttgatcacac ccgccacacc cgcagcagcc tgcgcatgcc cgatgttcga cttcaccgac   38640
cccaaccaca ccggcgtgtc accggcccgc tgcccgtacg tggcgagcaa cgcctgcgcc   38700
tcgatcggat cacccagcgt cgtgcccgtc ccgtgcccct ccaccacatc cacatccgcc   38760
acagacaacc ccgcacacgc caacgcctgc cgaatcaccc gctgctgcga cggaccattc   38820
ggcgccgtca acccattcga cgcaccgtcc tgattcaccg cactcccccg caccaccgcc   38880
aaaacccgat gaccacgacg ttcagcctcg gacagccgct ccagcagcaa aatccccacg   38940
ccctcggaca tgccggtgcc gtcggcagcc gacgcgtacg ccttgcaccg gccgtccggc   39000
gacagacccc gctgccgcga gaactccacg aacatgcccg gggtggacat gaccgtcacg   39060
cctccggcga gggcgaagga ggactcaccg gtgcgcagtg actggcaggc gaggtgcagt   39120
gccaccagcg acgacgagca cgccgtgtcg accgtcaccg cggggccctc gaagccgaag   39180
gtgtaggcga cgcgtccgga caggatgctt cccgcgttgc cgttgcccag gtagccggcc   39240
aggtcgtcgg ggaccgagag cagacgggtc gcgtagtcct gggacatgag gccggcgaag   39300
acgcccgtcc ggctgccgcg caacgtggcg gggtcgatgc ccgcccgctc caacgcctcc   39360
caggacacct ccagcatcaa ccgctgctgc ggatccatcg ccaacgcctc acgcggactg   39420
atcccgaaaa accccgcatc gaactccgcc gcaccctcca ggaaaccgcc ccggcgcgta   39480
tacgacgaac ccgccgccc cggctccgga tcatagaaag cctccacgtc ccaacccgg    39540 tcgaccggaa actcccccac cgcatcccga cccgacgcaa tcaactccca gaaatcctcc   39600
```

```
gccgactcca cacccccgg aaaacggcac gccatcccca caattgcaat cggctcctgc    39660
tcgcccgatt caatctgctg aagtcgacgc cgcacattga ggagatcggc agtaacgcgc    39720
ttgagatagt cgcggagctt ttcctcgtta gccatggacc ggtctcctcg acaagagaaa    39780
tcggaaatta aaaacacgc atgggactct cacaggctag agcgacgaga gcagcacaaa     39840 taccctaga taccccagac ccctgatgct cgatgaatgc cgctatagct agggggtatg    39900
gcgccagaca tg                                                        39912

<210> SEQ ID NO 4
<211> LENGTH: 60
<212> TYPE: DNA
<213> ORGANISM: Streptomyces avermitilis

<400> SEQUENCE: 4
ccatggaccg gtctcctcga caagagaaat cggaaattaa aaacacgca tgggactctc      60

<210> SEQ ID NO 5
<211> LENGTH: 3274
<212> TYPE: DNA
<213> ORGANISM: Streptomyces avermitilis

<400> SEQUENCE: 5
accggtcacc cggtattcca ttcggtgttg cagcacgcga cccactgcgc atcccactcg      60
tgaattgtgg accgccatcc ggggcacgga tgtctccagg aaggaactcc ttcaccctcg     120
cgaacaccac ctcagaatcc cacgatcatc agttaatcat caaagtcagc gaccttgaca     180
ctaccccgcc caccagggca aattcataac actgaccatc acctctgatg ctgatcaacc     240
cagcccgcac ggccgcgacc gcttttgctc aagcaatcga aatccccgag acacgctttc     300
ttggaaaaag gagaaataag aacatcatgc agggagtttc ctgtctgcac cccctcgga     360 aaccagaaga actcacgctc gtcgaccggg aaacacagtt ccgcgcgctg cggctggccc     420
ttaccgaatg cgcggccggc acggtgaaac tgctcgtcgc cgagggcgga atgggctgtg     480
gaaagagtac gttcctgggc gaggcactgc acaccgccgc cgcctccggc ttcgccgtcc     540
tgcgtgccgc cgggcttccc gcggaccacc ggcaacccct cggcgtactg cagcaactgc     600
tgaacgaccc cgcccccgag gacaccgccc gcaccgccgt ccgccccatg ccggtgcaac     660
acgtccgcgg cgccctcgaa cgcctcgccg ccggcgcccc gctggcgatc ggcatcgacg     720
acgtacagga cgcggacccg gagtcgctgc actgtctgat cgcctcacc cgccactccc     780 ccacctcgcg gatcctgctg ctgtgcaccg ccctggcgtg cagtccggcc gccgacccgg     840
tactcgaagc cgagctgatg cgtcagaccg ccttcgaacg catcacgctg gactgcctgt     900
ccctggacgg agtgaccggg ctggtctcgg accgctgcgc gcggcccacg cgccccccgc     960
cggcggacta ctgcctgacc gtcaccgggg gcaacccgct gctgctgcgg gccctgctcg    1020
aagagcacag cgaggccgac gccccctcgg cacccccgccc ggcggagccc tccgcgctgc   1080
actccccgcc gcaggccgcc ccgccgcgcc cggtcgtcgg cggccgcttc taccagtccg    1140
tactggcctg cctgtccccgc acggagacgg cgatcaggca gacggccggc gccctcgccg    1200
tcctcggcgg gcgtgcgcgc gccgacctgc tccccaact gctcggcgcg agtccgcgt      1260 cggtcacccg ggggctgcgt gcgctggagg cgacgggct gaccacctcc ggccgttcc      1320 ggcacccggt ggccgaggcc gccgcgctcg acgcactgga cccgagccgc cgtgcccacc    1380
tgcaccgccg agcggcggcg ctgcagcacc acgacgcgc ggcgccgcgg gacgtcgccc     1440
gccaccttct cgcggcccgc catgcggcgg gccctgggc ggtgtccgtg ctgcgtgacg    1500
```

-continued

```
ccgccgagca gtcgctggcg caggacgacg tggcgtcggc ggtctcctgc ctggaactcg     1560
cctacggggc ctgtgtccgg gaacgggaac gtccggagat caggatcagg ctcgccgccg     1620
ctttcgggcg caccaacatc gcggtggcgg aagagcacct cgccgacctg gtcgccacct     1680
tgcgggaagg agaattgacc ggccatcaga cggctttact cgtccctctg ctcgtcaacc     1740
acggccgcct cggcgaagcg cgggaggcga tggaccggct caacgccgcc gacgacgcgc     1800
gcggcctgtg cgcggacggc ggcttcccga tggccgctcc gtggccgtcg accgcacacc     1860
tcgccgcacg ccgcgatccc gccgcgcgcc gcgatcccgg cacccgccgc gatcccgccg     1920
acaagccgtt cctgccccgg cagtccggtg ccccgcagcc ccggccggag acggccgtg      1980
gccagcagcc gacagcggcc ttgtgggccc tgcccggaaa cggcaccagc gaggcggccg     2040
cacacgccgc ggaacaggta ctgcggtcct ccccgctcac cgacagcacc ctcgtgctcc     2100
tggtgaacgc cgtgcggatc ctcgcccgca cgggccggta cgacaccgcg acatctggt      2160
gccaccgcct gctcggcgag gccacccgtc gccgttgtcc cggctggcag gcgcacctcc     2220
tggcggtgcg ggccgaactc tcgctgtgcc gtggcctgct cgccgacgcc aaggagtgcg     2280
cccagcgcgc actgacacac gtaccggggc acagccgcag cgtcttcgcg ggcggtccgc     2340
tggcctgcca ggtcctcgcc tgcaccgcga tgggacgcta cgacaagcc acgcaactgc      2400
tcagccatcc ggttcccgag gcgctgttcc acagtgtgta cggcctgggg tacctgcggg     2460
cccggggcca tttccacctg gccatgaacc gcctgcccgc cgccgtccgc gacttcctca     2520
ccgccggccg ggtggcgcgg gagtggggac tggaccatcc ggtgctgctg ccctggcgta     2580
cggacgccgc ggaggcgttc ctccggctcg gggaaacgaa gagggccgac caactcctca     2640
ccgaacagct cgtctccccg cacagcggca accggtacgt ccgcggcacc gcgctgcgcc     2700
tgcgggccca gaccgcggcg ccggcggaac ggctccggct gctgagcgag gcggtcagtg     2760
acctccagag ctccggcgac cgcctggcgc tggcccgcgc actggccgat ctcggcgccg     2820
cgtatcacag ccggaacgag cccgtacggg cgagcgccac ggtccgccgc gcctggcagc     2880
tggccaagga gtgcggagcc caggccctgt gcgacagcat cctgcccagt cgcggcacca     2940
aggaccgggg gcccgacgga agggcggccg cgaccgaggc cctgctgagc gagtccgaga     3000
tgcgagtcgc gacactggcg gcgggcggca acaccaaccg tgagatcgcc ggccggctct     3060
gcgtcaccgt cagcacggtc gaacagcatc tgacgcgggt ctaccgcaaa ctgaacatca     3120
cccgccgcag ggagctgccg accgtctctg gacacctcgc ggaccaggcc aactgaccac     3180
gggagggggg gcgtcccggc cgacgtgtgc tcgtcttccg cctcacgaca tggcgggcgc     3240
gatgcacagc cccccactcg catccaccaa ctga                                 3274
```

<210> SEQ ID NO 6
<211> LENGTH: 11041
<212> TYPE: DNA
<213> ORGANISM: Streptomyces avermitilis

<400> SEQUENCE: 6

```
ctgcagccgg cccgcacccc cacccgcgcc cccgacgcc tcctccaaaa tcacatgcgc       60
attcgtccca ctcaccccga acgcagacac ccccgcacgc cgcagccgac cctccacccc     120
cggccactcc acctcatccg ccaacacacg aaccgaccca ctcgaccaat ccacctgcga     180
cgacggctca tccacatgca acgtccgcgg caacacccccc gcccgcaacg ccatcaccat     240
cttgatcaca cccgccacac ccgcagcagc ctgcgcatgc ccgatgttcg acttcaccga     300
```

```
ccccaaccac accggcgtgt caccggcccg ctgcccgtac gtggcgagca acgcctgcgc      360
ctcgatcgga tcacccagcg tcgtgccgt cccgtgcccc tccaccacat ccacatccgc      420
cacagacaac cccgcacacg ccaacgcctg ccgaatcacc cgctgctgcg acggaccatt    480
cggcgccgtc aacccattcg acgcaccgtc ctgattcacc gcactccccc gcaccaccgc    540
caaaacccga tgaccacgac gttcagcctg gacagccgc tccagcagca aaatccccac    600
gccctcggac atgccggtgc cgtcggcagc cgacgcgtac gccttgcacc ggccgtccgg    660
cgacagaccc cgctgccgcg agaactccac gaacatgccc ggggtggaca tgaccgtcac    720
gcctccggcg agggcgaagg aggactcacc ggtgcgcagt gactggcagg cgaggtgcag    780
tgccaccagc gacgacgagc acgccgtgtc gaccgtcacc gcggggccct cgaagccgaa    840
ggtgtaggcg acgcgtccgg acaggatgct cccgcgttg ccgttgccca ggtagccggc    900
caggtcgtcg ggaccgaga gcagacgggt cgcgtagtcc tgggacatga ggccggcgaa    960 gacgccgtc cggctgccgc gcaacgtggc ggggtcgatg cccgcccgct ccaacgcctc   1020
ccaggacacc tccagcatca accgctgctg cggatccatc gccaacgcct cacgcggact   1080
gatcccgaaa aacccgcat cgaactccgc cgcaccctcc aggaaaccgc cccggcgcgt    1140
atacgacgaa cccgccgcc ccggctccgg atcatagaaa gcctccacgt cccaacccg    1200 gtcgaccgga aactccccca ccgcatcccg accgacgca atcaactccc agaaatcctc    1260
cgccgactcc acacccccccg gaaaacggca cgccatcccc acaattgcaa tcggctcctg    1320
ctcgcccgat tcaatctgct gaagtcgacg ccgcacattg aggagatcgg cagtaacgcg   1380
cttgagatag tcgcggagct tttcctcgtt agccatggac cggtctcctc gacaagagaa    1440
atcggaaatt aaaaaacacg catgggactc tcacaggcta gagcgacgag agcagcacaa    1500 ataccctag ataccccaga cccctgatgc tcgatgaatg ccgctatagc tagggggtat    1560
ggcgccagac atgaattcac agcgtttcgg cggccggctg gcgcttgtca caggtgcagg    1620
cggtggcatc gggcgggcga ccgcctgcgc tctcggatcg gccggggcgc gagtggtgtg    1680
cgtggaccgg gacggccgcg gcgccggggt gacggccgac ctggcccgga cgcgggggcgc    1740 gcgggcggcc tggcccgagg tggccgacgt gtccgacgga gcggcgatgg agcggttcgc    1800
cgagcgcgtc gccgagacgt acggggtcgt ggacctgctg gtgaacaacg ccggcatcgg    1860
catggcgggg cgttttctcg acacgtccgt cgaggactgg cagcgcaccc tgggcgtcaa    1920
cctctggggt gtcattcatg gttgccgcct catcggccgg cagatggcgg agcgcgggca    1980
gggcgggcac atcgtgacgg tggcgtcggc ggcggcgttc cagccgacgc gggcggtccc    2040
cgcgtatgcc accagcaagg cggcggtgct gatgctgagc gagtgcctgc gcgcggagtt    2100
cgcggagttc ggggtcggag tgagcgtggt gtgcccgggc ttcgtccgta cgtcgttcgc    2160
gtcggcgatg catttcgccg gtgtgccccg gctggagcag gagcggctgc gggcgctgtt    2220
cgccggtcgc ggatgcagcg cggagaaggt ggccgcggcg gtactgcggt cggtggcgcg    2280
cgactcggcc gtggtgaccg tgacggcgga agcgcggctg tcacggctga tgagccgctt    2340
cacgccacgc ctgcgcgccg cggtggcgcg gatggatccc ccttcgtagg ctggcgggg    2400 atcccctcct tgccttcgaa catcttccga cgatgggcag tgagagatgt cagatcattt    2460
tctcttcatg agtgcgccgt tctggggca tgtgttcccc agtctcgccg tggcggagga    2520
gctcgtgcac cggggccacc acgtcacctt tgtgacgggc gcggaaatgg ccgatgcggt    2580
gcgttccgtg ggcgctgatt tcctgcgta cgagtccgcc ttcgagggtg tcgacatgta    2640
ccggctgatg accgaggccg agccgaacgc catccccatg acgctgtacg acgagggcat    2700
```

-continued

```
gtccatgttg cgttcggtgg aggagcacgt cggcaaggac gttccggacc tggtggccta    2760
cgacatcgcc acctccctca cgtgggtcg tgtcctcgcc gcctcctgga gcaggccggc    2820
catgacggtc attcccctgt tcgcgtccaa cgggcgcttc tccacgatgc agtcggtatt    2880
ggatccggat tccgctcagg tcagtgcgcc gccgccgcgc ttctcggagc agatggagtt    2940
gttcggcctc ggggcgctgg tgccgcgcct cgcggagctg ctcgtttccc ggggtatcac    3000
ggaaccggtc gacgatttcc tttccggacc ggaggacttc aacctggtgt gtctgccgcg    3060
cgccttccag tacgcgggcg acaccttcga cgagcggttc gccttcgtcg accatgtct    3120 gggtaagcgc aggggtctgg gcgagtggac accaccgggc agcgggcatc cagtggtgct    3180
catctccctc gggaccgtgt caaccggca gctgtccttc ttccgcacgt tcgtccgggc    3240
gttcaccgac gtccccgtgc acgtcgtgat ctcgctcggc aaggggggtcg accccgatgt    3300 gctgcggccg ctgccgccga atgtcgaggt gcaccggtgg gtgccgcacc atgcggtgct    3360
ggagcatgcc agggctctgg tcacgcacgg cggtaccggc agtgtgatgg aggcactgca    3420
cgcagggtgc ccggtgctcg tcatgcccct gtcgcgggac gcgcaggtga ccggccggcg    3480
gatcgccgag ctggggctgg gtcgtatggt gcagccggag gaggtcacgg cgacgacgct    3540
gcgccggcac gtgctggaca tcatctccga tgacgcgatc acccgacagg tcaggcagat    3600
gcagcgggcc acgtcgagg cgggcggcgc cctgcgggca gcggacgaga ccgagcggtt    3660
tctgcgccgg acgcgccgtc actgaccggc agctcgggcc gggcggtgag tggctcccac    3720
agggttcggt tctccacgta ccactgaacg gtctgtgcca gccctcctc gaagggcacg    3780 cggggcgcgt aaccgagctc ggcggagatc ttgctgatgt ccagcgagta gcgccggtcg    3840
tgccccttgc ggtcggtcac gggttcgacc atcgaccagt ccacgccgag caggtccagg    3900
agccgggcgg tgagctcacg gttggacagc tccgtcccgc ctccgatgtg gtagatctcg    3960
ccgggcctgc cgcgttcggc gaccagggcg atgccacggc agtggtcgtc cacgtgcagc    4020
cagtcgcgga cgttttcgcc gtcgccgtac aagggcacct tcgtgccgtt cagcagatgg    4080
gtgacgaacc gcgggatgag tttctccggg aactggtggg ggccgtagtt gttcgagcat    4140
cgggtgatga tcactggtag gccgtgcgtg cggtggaagg accgggcgag caggtcggag    4200
gacgccttgg acgcggagta gggcgagttc ggctccagcg gggcgtcctc ggtccacgag    4260
ccggagtcga tggagccgta gacctcgtcc gtcgagatgt acacgaagcg gtccacggcg    4320
gcgtcggtgg cggcgcggag cagggtgtga gtgccgagga cattggtgcg tacgaactcg    4380
gcggcgtcgg ccacggaccg gtccacgtgt gactccgccg cgaagtggac caccatgtcg    4440
gagccgtcca tcaggtccgc gaccaagggc ccgtcgcaga tgtcgccgtg cacgaagatc    4500
agggatgggc ttcccaggac cggtgcgagg ttctccaggc gacccgcgta ggtcagcttg    4560
tcgagcacca cgacctcggc accggtgaac gccggatacg cgcccgtcag caaccgccgt    4620
acgaaatggg aaccgatgaa accggcgccg cccgtcacga gtaggcgcat cccgggctcc    4680
tcaccgcggc ttccgccgca atactcatca gatactcgcc gtagcggag ccggccagtt    4740 cgacccccgcg cagatagcag tcgtccgcgt cgatcagacc catccggaag gcgatctcct    4800
cgagacaggc gatccgtact ccctggcgct tctccaggac ctgcacatac tgccggcgt    4860 gcatcagcga gtcgtgcgtc cccgcatcga gccaggtgaa gccccggccc aggtccacca    4920
gccgggcccg cccctcggcg aggtaggccc tgttgacgtc ggtgatctcc agctcgccgc    4980
gggccgacga gcggatgccc cgggccacct cgatcacgtc gttgtcgtac aggtacaggc    5040
```

```
ctgtgatcgc caggttggac cggggggcgg tgggtttctc ctcgacggac agcagctttc    5100
cggaggcgtc gacctctccg actccgtacc gttcgggatc cgtcaccgcg tatccgaaca    5160
acacacagcc gtcgacatcg cgggtgtggc tgcgcagcag gtgcgaaaag cccatgccat    5220
ggaagatgtt gtccccaagg acaagggaca cctgatcctg accgatgaaa tcggcgccga    5280
tgaggaatgc ctcggcgatt cctcccggtc gctgctgcgc ggcgtagtcg atgttcagcc    5340
cgaggcggct tccgtctccg agcagtctcc ggaattgttc gagatgatcg ggtgaggaaa    5400
tcaccaggat gtcttttatg ccgccgagca tcaacacgga gagcgggtag tagatcatgg    5460
gtttgtcgta gacagggagc agctgcttgg aaagggcacg ggtcaacggg taaagccgag    5520
agccggttcc ccccgcgagc acgattccct tcatgtcgga ctccccgcag tcgacgttat    5580
atatctctgc cgtctgcccg acggtaccaa gtggcgaaaa acgcaccagg aattcgagcg    5640
ccgctagggg gaagggctca agaagatagg ggccaccaga tggggcggtt ttcggtgtgc    5700
ccgccccggc cgaccggaat actgaagagc atgctgacga ctgggatgtg cgaccgaccg    5760
ctggtcgtcg tactcggagc ctccggctat atcgggtcgg ccgtcgcggc ggaactcgcc    5820
cggtggccgt tcctgttgcg gctggtggcc cggcgaccgg gcgtcgttcc gccgggcggc    5880
gccgcggaga ccgagacgcg tacggccgac ctgacggcgg cgagcgaggt cgccctcgcc    5940
gtgacggacg ccgacgtggt gatccacctg gtcgcgcgcc tcacccaggg agcggcatgg    6000
cgggcggcgg agagcgatcc ggtggccgag cgggtgaacg tcggggtgat gcacgacgtc    6060
gtcgcggccc tgcggtccgg gcgccgcgcc gggccgcccc cggtggtggt gttcgccggg    6120
tcggtctacc aggtgggccg cccgggtcgg gtcgacggca gtgagccgga cgagcccgtg    6180
acggcctatg cccgtcagaa actcgacgcc gaacggacgt tgaagtccgc cacggtcgag    6240
ggtgtcctgc gggggatctc gctgcggctg cccaccgtct acggcgcggg gccgggcccg    6300
cagggcaacg gcgtcgtgca ggcgatggtg ctccgggcgc tcgccgacga ggccctcacc    6360
gtgtggaacg gaagcgtggt ggagcgtgac ctggtgcatg tggaggatgt cgcgcaggcc    6420
ttcgtgagct gcctggcgca cgcggatgcg ctcgccgggc ggcactggct gctcggcagc    6480
ggtcgtcctg tgaccgtccc gcacctcttc ggtgccatcg ccgccggcgt gtccgcccgc    6540
accgggcgcc ccgcggtgcc cgtgaccgcg gtggaccctc cggcgatggc gacggcggcg    6600
gacttccacg ggaccgtcgt cgactcctcg gcgttccgcg cggtcaccgg gtggcggccg    6660
cggctgtcgc ttcaggaggg cctggaccac atggtggcgg cttacgtgta gcgccggggt    6720
ggcggccggg cccgggcggt gacggcccgg atcgggtcg gccgtcacag cttctcgtcg    6780
aggccgcggc tcgcgcggta ctccggcaac atgccgcgtc gcagggcctg ctggagagtc    6840
ggcgcgcgcc ggtcgcgctc ggagaggatc ggtgcccgcc cgaggtggtg gccgaggggc    6900
agggcgaggt ccggatcctc gggcgagagg gcgtgttcgt tctgcggaac gtagccgctc    6960
gacatcaggt acaccatcgc cgtgtcgtct tccagcgcca cgaacgcgtg cccgaccccg    7020
atcggcaggt agacggaacg gaagcgctcc tggtcgagga ggaccgagtc ccactgcccg    7080
aaagtcggtg agccggtgcg caggtcgacg acgaagtcca gggcccgtcc ccgggcgcag    7140
tggacgtact tggcctggcc gggtggtgtc gcggtgaagt gcacgccgcg gacgacgccg    7200
cggcgcgaga cgctctggca ggtctgcgcg gtgggaaacc ggtgcccgac ggcctcgctg    7260
aggaccggtt cctggtaggg ggtgacgaag agcccgcgct cgtcggggaa gaccgtcggg    7320
gtgaattcga cggcgccctc gacgacgagc ctccggaccg tgacaccggc ggcggtggcc    7380
cgggcgcccg cgggcggggc gggccggtcg gcggagctcc ggcgaggccg gccaagggtc    7440
```

```
atcgctgcac tctctctgtc gtgcgggttg tcatacgggt agtcgtacgg gccggttccg   7500
gagtcacagc tcgacggcgc gggtggtgag cagggacagc agggtgcggg cctgcacgtt   7560
cacgtaacgg ccgtaccgca gcagctgggt cagctggccc ggggtgcacc agcggtaccc   7620 cggggggcggg tcgttcggcg cctggctctc gtcggcctcg acgaacaggt agcgcgcctg   7680
tgcgtgcaga aagcgaccgc cctcctccga gtggaccgcc gcgtagcgga tgcggtcggg   7740
cgcggcctcc agcaccaggt cgaggaagcg cggcctggcc ggtcccgtga ggtgggcgta   7800
gttgcgcggg gtgtactgga ccgtcgggcc gagttcgatc gtgtcgagga agccgccctc   7860
gaccctgccg tgggcgagca ggtgcggtac gccgccgatc cgccgggtca ggaaggcggt   7920
gatgccgtgg ccgcacggtt cgatcagggg ctgggtccag gcggcgacct cccgttggga   7980
ggcctcgaca cggaccgcga ccacacggaa gtaccggtcc gcgtggtggg cgatggactc   8040
cgcgcccgtg gtccagccgg ggatgccggc caggggcacg cggcgggcgt gcacggagtg   8100
ccgggagcgt tcggcggcgt accaggagag cagttcggcg tcgctgtgca gggccgcggg   8160
ctcgtcgaac ggggtgggaa ggcaggcgag gaccgtgcgt gcgtccatgt tcaccaggtt   8220
gtcccggtgc atcagttcgc cgatctgccc cagtgtcagc cagcggaagt cgtcgtccag   8280
tggtacgtcc tcgtcggtct ccaccacgat gttgcggttg aacttccggt ggaaccaggc   8340
tccgtgctcg gactggagga cgtcgaccac cacggtggcg cgccggggct gtgtgaagta   8400
ctcgaggtac ttcacggcgg cgccccgtg gaccttggtg tagttgctgc gcgtggcctg   8460
cacggtgggc gacagctgga ccaggttgat gttgccgggc tccatcttgg cctgcatcag   8520
gaagtgcagg accccgtcga acttcttggc gaggatgccg aggatgccga tctcgggctg   8580
gtggatgatg ggctgctgcc attccgggaa gggctgttca ccgcctcgga cgtgcagtcc   8640
ctccacggag aagaaccggc cgctgcggtg gccagattg ccggttccgg ggtgaaacga   8700
ccaggcgtcc atcccgtgga aggggatgcg ctcgacccgg aaccggtggg ccccggaccg   8760
ccgcgtccac cagccggtga acgcgtcgag ggacgtccgg cgccggtgtc gcccacggcg   8820
gcggagcggg cgaggcacgc gggcagggcg gcgtcgtgcc gcgcggtgag cggtgctggg   8880
ctcggtgtgg tcggcatcgg ctcgtacgct catgcacccc acgtcatgta gatcaccggt   8940
ggctcgcggc cgggcagttg gcgcagtggg gcgtggtcga ggccgaacgc ctcgctcagc   9000
gccctggtct cccccggcca tttggggtgg gtgagttcgt cgaaggcgag gatgctgccc   9060
ctggtcaggt gcggtgtgat gacgtccagc agttcgcgcg tggggcggta gaggtccagg   9120
tcgaagtagg ccagcgcgat gacggtgtgc gggtgttccg ccaggtattg gggcaccgtt   9180
tcgcgtacgt cgccctggac cacgaaggaa cgctgggtgt ggccgtaggg ttcgttcgcc   9240
tcgtgcgccg cgagcacctg ccgcaggtgc tccacttcgc cgtccggcac ggcgaaccgc   9300
ccagggaccg cgctggtgct gacctcgtcc gcctcgtcga tgtcggggaa gccggtgaac   9360
gtgtcgaagc cgatgacgcg gcgcagcgag ttgtacggct catagatgct gcgcagcgcg   9420
gtcagcgtgg cgaggtgccg tccgtgcaga acgccgaact ccatgatgac gccggggact   9480
tccggcagca tgcggtacag cgcgtccatg gagagcaggt cggcgagctg gttgcgccgc   9540
atgtagacgg acaggttgtc gatcaggtac ttccggcggga tcgggctgtc gacgaggagc   9600
ttggtcagct gctcgcgggc agcgcgttcc tgctcggact cgtgcggcac gatccgggga   9660
tcggtgaact cccgctcggt catggaggcc tttcctttca tgggtcggta ccgggcgcgc   9720
cggacgtgcc ggtcgtaccg ggcgtgccgg cgggcacgac gctgtcggt caggacagcc   9780
```

```
aggcgtcggg ggcggatccg ccgcggccga ccgggggaa cagctcctcc aggcgggcca    9840
ggacgggctc gggcagcggg gtgcgcaggg cgtgcagtgc cccgtccacg tgctgttcgg    9900
tgcgcggccc gatgaccagc ccggtcacgc cgggccgcga cagcacccag gccatgccga    9960
catgggcggg gtcgaggccg tggtccgcgc acacgtcctc gtacgccgcg atggtggtgc   10020
ggtggtgctc cagggcctcg acggcccggc cctgtgccga cttgaccgcg gtgttctccc   10080
gcgtcttgcg caggacaccg ccgagcaggc cgccgtgcag tggcgaccag accaggacgc   10140
cgacaccgta ggcggacgcg gcggggatga cttccagctc ggcgtgtcgg gtcacgaggt   10200
tgtagacgca ctgctcggag gcgaggccca gggcgttgcg ccgccgggcc gcctcctggg   10260
cggaagcgat gtcccagccc gcgaagttgg aggagccgac gtagcgcacc ttgccctgcg   10320
tgatgagcag gtccatcgcc tgccacacct cgtcccagcc ggcgcggcgg tcgatgtggt   10380
gcagctggta caggtcgatc cagtcggtgc gcagtcggcg cagcgaggcg tcgcaggcgg   10440
ccacgatatt gcgtacggac agtccgtgat cgttggggcc gctgcccatc ggatcgccga   10500
ccttggtggc cagcaccacc tgctcacgcc gggcggggcg gtccgccagc cacctgccga   10560
tgacctcttc ggtgtacccc ttgtggacgc gccagccgta ggtgttggcg gtgtcgaaca   10620
gggtgatgcc ctgagccagg gcgtgatcca tcagtcggcg cgcttcgggc tcctccaccc   10680
gtccgccgat gttgaccgtt ccgagcgcca gtcggctgat cctcagccgg gtcctgccca   10740
gttcggtgtg gaggggagca ctgctgttgc tgtcggactg gacgggtgcg ggctcggccg   10800
tcgtaggcat catcgatcag tcgacactcc ctcgtgcgtg agcggcgggc gctcgagcag   10860
gaccctgacc tgaggcccag gaggctaccg gcgatcatgc gatacaggca gccgctcgat   10920
ggtgggacac gggctgccgt cgccgggcat aggggctgat gggggttgtc cggtgcgggt   10980
ccggctgaca gcttcgtgga caccaagttg atccagttga tccactccga aaggcagagg   11040
c                                                                   11041
```

STRAIN BELONGING TO THE GENUS *STREPTOMYCES* AND BEING CAPABLE OF PRODUCING NEMADICTIN AND PROCESS FOR PRODUCING NEMADICTIN USING THE STRAIN

A strain having C-13 substituted nemadectin producing activity belonging to genus *Streptomyces* and a method for manufacturing c-13 substituted nemadectin using the same

TECHNICAL FIELD

The present invention relates to a strain having C-13 substituted nemadectin producing activity belonging to genus *Streptomyces* and a method for manufacturing C-13 substituted nemadectin using the same. More particularly, the present invention pertains to the method for manufacturing C-13 hydroxylnemadectin and C-13 glycosylnemadectin using the microorganism belonging to genus *Streptomyces* having C-13 substituted nemadectin producing activity, and the microorganism strain belonging to *Streptomyces cyaneogriseus* subspecies *noncyanogenus*.

BACKGROUND ART

A series of compounds having benzofuran ring structure has excellent antiparasitic activity and antiinsect activity. Among them, avermectin and milbemycin are now practically used. Four components, α, β, γ and δ, of nemadectin, which has benzofuran ring structure produced by *Streptomyces cyaneogriseus* subspecies *noncyanogenus*, are known, and the C-13 position thereof has no substituent and is saturated as shown in the following structure.

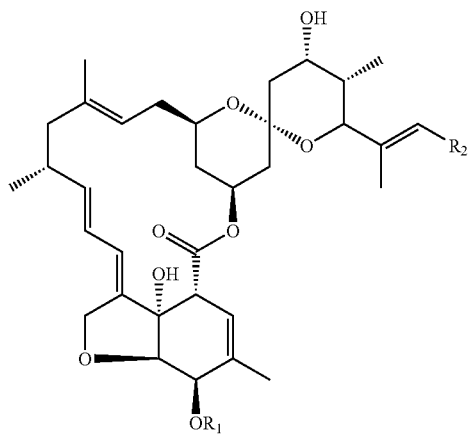

Nemadectin α $R_1$=H $R_2$=CH(CH$_3$)$_2$
Nemadectin β $R_1$=H $R_2$=CH$_3$
Nemadectin γ $R_1$=CH$_3$ $R_2$=CH$_3$
Nemadectin δ $R_1$=CH$_3$ $R_2$=CH(CH$_3$)$_2$ A reason why the C-13 position of nemadectin is saturated is that a module 7 of nemadectin polyketide synthetase (nemadectin PKS), which is involved in the formation of nemadectin aglycon moiety, is constructed by the structure of KS-AT-DH-ER-KR-ACP. It is difficult to construct stereoselective modification in the saturated C-13 position by chemical synthesis. Although increasing antiinsect activity and antiparasitic activity can be expected by an addition of sugar moiety as like in avermectin of the following structure, a production of derivatives by chemical synthesis has not been made.

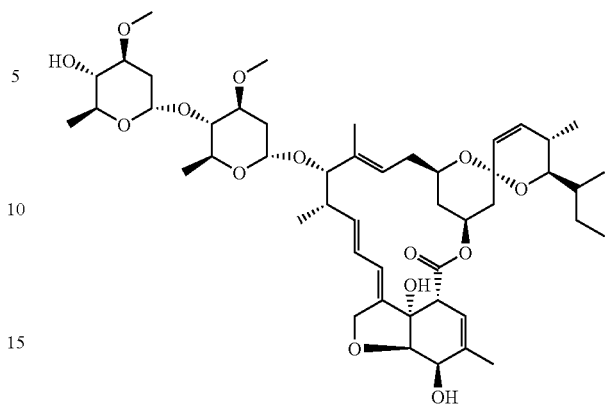

As described in the above, although stereoselective introduction of hydroxyl group and glycosylation of the hydroxyl group of nemadectin at C-13 position by chemical synthesis might be difficult to perform, as a result of extensive studies, we have succeeded in preparing C-13 glycosylated nemadectin producing microorganism by means of the molecular genetic technology and obtaining efficiently nemadectin with stereoselective glycosylation.

The present invention was completed based on such the knowledge. An object of the present invention is to provide a microorganism belonging to genus *Streptomyces* having C-13 glycosylnemadectin producing activity by the molecular genetic technology. Another object of the present invention is to provide a microorganism strain belonging to genus *Streptomyces* having C13 substituted nemadectin producing activity, which can be used for obtaining effectively nemadectin with stereoselective glycosylation and expected to improve the biological activity thereof.

Further object of the present invention is to provide a method for manufacturing C-13 substituted nemadectin comprising introducing DNA of a microorganism, which produces nemadectin analog, into the nemadectin producing microorganism belonging to genus *Streptomyces* and accumulating C-13 hydroxylnemadectin and C-13 glycosylnemadectin and collecting the same.

DISCLOSURE OF THE INVENTION

We have prepared the C-13 hydroxylnemadectin producing microorganism strain by modifying gene groups of nemadectin aglycon biosynthesis in order to obtain C-13 hydroxylnemadectin, which can be modified for adding the sugar moiety by chemical synthesis, and generating a hybrid polyketide synthetase (hybrid PKS) with nemadectin PKS and avermectin polyketide synthetase (avermectin PKS). Further, we have improved a productivity of C-13 hydroxylnemadectin as a result of stimulating transcription of avermectin PKS gene by introducing aveR gene which was involved in the transcriptional control of avermectin PKS.

The present strain *Streptomyces cyaneogriseus* subsp. *noncyanogenus* ΔnemA4::vph attB$_{TG1}$::aveA4-aveA3-aveE attBφ$_{c31}$::aveR was deposited in the International Patent Organism Depositary, National Institute of Advanced Industrial Science and Technology, AIST Tsukuba Central 6, 1-1, Higashi 1-chome, Tsukuba-shi, Ibaraki-ken, 305-8566 Japan based on Budapest Treaty on the International Recognition of the Deposit of Microorganisms for the Purposes of Patent Procedure as accession number FERM BP-8395 on Jun. 6, 2003.

Further, we have prepared the microorganism strain, to which aveBI-BVIII gene group involving in glycosylation of avermectin and oleandrose biosynthesis was introduced, and prepared the C-13 glycosylnemadectin producing microorganism strain.

The present strain *Streptomyces cyaneogriseus* subsp. *noncyanogenus* ΔnemA4::vph attB$_{TG1}$::aveA4-aveA3-aveE attBφ$_{c31}$::aveR attB$_{R4}$::aveB1-BVIII was deposited in the International Patent Organism Depositary, National Institute of Advanced Industrial Science and Technology, AIST Tsukuba Central 6, 1-1, Higashi 1-chome, Tsukuba-shi, Ibaraki-ken, 305-8566 Japan based on Budapest Treaty on the International Recognition of the Deposit of Microorganisms for the Purposes of Patent Procedure as accession number FERM BP-8394 on Jun. 6, 2003.

The present invention relates to a method for manufacturing C-13 glycosylnemadectin comprising culturing a microorganism strain belonging to *Streptomyces cyaneogriseus*- subsp. noncyanogenus, producing and accumulating C-13 glycosylnemadectin and isolating C-13 glycosylnemadectin from the cultured mass. Further, the present invention relates to the microorganism strain belonging to *Streptomyces cyaneogriseus* subsp. *Noncyanogenus* and having ability to produce C-13 hydroxylnemadectin and C-13 glycosylnemadectin.

As described hereinabove, a report, wherein C-13 hydroxylnemadectin and C-13 glycosylnemadectin were produced and accumulated by introducing DNA of the microorganism, which produced nemadectin analogous compounds, into the nemadectin producing microorganism belonging to genus *Streptomyces*, has not been known.

Consequently, the present invention provides the microorganism strain belonging to *Streptomyces cyaneogriseus* subsp. *noncyanogenus* and having ability to produce C-13 glycosidated nemadectin.

Further, the present invention provides the microorganism strain belonging to *Streptomyces cyaneogriseus* subsp. *noncyanogenus* and having ability to produce C-13 hydroxylnemadectin.

Further, the present invention provides a method for manufacturing C-13 hydroxylnemadectin comprising culturing a microorganism strain belonging to *Streptomyces cyaneogriseus* subsp. *noncyanogenus* and having ability to produce C-13 hydroxylnemadectin, producing and accumulating C-13 hydroxylnemadectin in the cultured medium and isolating C-13 hydroxylnemadectin from the cultured mass.

Further, the present invention provides a method for manufacturing C-13 glycosylated nemadectin comprising culturing a microorganism strain belonging to *Streptomyces cyaneogriseus* subsp. *noncyanogenus* and having ability to produce C-13 glycosylated nemadectin, producing and accumulating C-13 glycosylated nemadectin in the cultured medium and isolating C-13 glycosylated nemadectin from the cultured mass.

Further, the present invention provides a microorganism strain belonging to *Streptomyces cyaneogriseus* subsp. *noncyanogenus*, maintaining gene groups of avermectin aglycon biosynthesis of *Streptomyces avermitilis* and having ability to produce C-13 hydroxylnemadectin, and a method for preparation of the microorganism.

Further, the present invention provides a microorganism belonging to *Streptomyces cyaneogriseus* subsp. *noncyanogenus*, maintaining gene groups of avermectin aglycon biosynthesis of *Streptomyces avermitilis* and having ability to produce C-13 glycosylated nemadectin, and a method for preparation of the microorganism.

Further, the present invention provides a nemadectin non-producing microorganism strain belonging to Streptomyces cyaneogriseus subspecies noncyanogenus and inserting viomycin resistant gene in the region coding nemadectin aglycon biosynthesis genes nemA3-4 operon KS10 (KS10 insertion mutant).

Further, the present invention provides a microorganism strain belonging to *Streptomyces cyaneogriseus* subspecies *noncyanogenus*, maintaining avermectin aglycon biosynthesis genes aveA3-4 of *Streptomyces avermitilis* in the KS10 insertion mutant, and having ability to form a hybrid PKS with NemA1-2 and AVES3-4.

Further, the present invention provides a microorganism strain belonging to *Streptomyces cyaneogriseus* subspecies *noncyanogenus* and having ability to form a hybrid PKS with NemA1-2 and AVES3-4, wherein the microorganism strain maintains a regulator gene aveR of avermectin biosynthesis genes of *Streptomyces* avermitilis.

Further, the present invention provides a microorganism strain belonging to *Streptomyces cyaneogriseus* subspecies *noncyanogenus* and having ability to form a hybrid PKS with NemA1-2 and AVES3-4, wherein the microorganism strain maintains a regulator gene aveR of avermectin biosynthesis genes and an avermectin glycosylation and an oleandrose biosynthesis genes aveBI-BVIII of *Streptomyces avermitilis*.

BEST MODE FOR CARRYING OUT THE INVENTION

Figure 1:
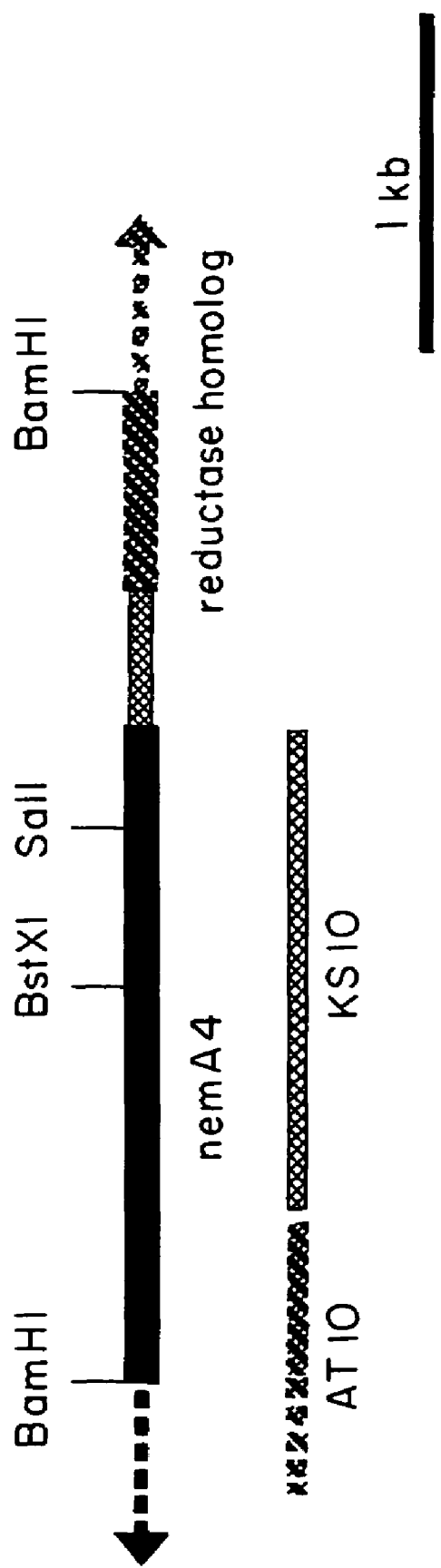
FIG. 1 is a restriction map of 3.0 kb fragment containing KS region of nemadectin PKS module 10. Arrow indicates a direction for transcription.

The present invention will be explained concretely by following examples, but the present invention is not limited within the description of these examples.

EXAMPLE 1

Obtaining *Streptomyces cyaneogriseus* subsp. *noncyanogenus* NRRL 15773, to which viomycin resistant gene (viomycin phosphotransferase: vph) was inserted into KS region of nemadectin PKS.

(1) Subcloning of DNA Fragment Coding Nemadectin PKS, KS 10

A cosmid DNA containing DNA coding a KS domain (NEM-KS10) of the module 10 in the cosmid DNA containing nemadectin aglycon synthetase gene was digested by a restriction enzyme BamHI (TAKARA BIO INC., Japan) and was electrophoresed with agarose gel. A DNA fragment 3.0 kb containing KS 10 region was isolated and purified by using a gene clean II kit (Bio101 Inc., US). In addition, a plasmid pUC 19 (TAKARA BIO INC., Japan) was digested with BamHI and was dephosphorylated by using alkaline phosphatase (Calf intestine) (TAKARA BIO INC., Japan). The 3.0 kb fragment containing NEM-KS10 and the BamHI digestion product of pUC19, each about 0.1 μg, were ligated by reacting at 16° C. for 16 hours with using Ligation High (TOYOBO CO. LTD., Japan).

The DNA ligation product 10 μl and competent cells of *E. coli* DH5α (Nippon Gene K.K., Japan) were contacted to perform transformation. LB agar medium 20 ml containing ampicillin 50 μg/ml (Wako Pure Chemicals Inc., Japan) was used for selection of transformant strains. Aqueous solution of isopropyl-β-D-thiogalactopyranoside (IPTG) 0.1 mol/lit. and dimethylformamide (Nacalai Tesque Inc., Japan) solution of 2% 5-bromo-4-chloro-3-indolyl-β-D-galactoside (X-gal, Nacalai Tesque Inc., Japan), each 50 μl, were previously smeared. Since a colony of the transformant maintaining a recombinant plasmid is defective in β-galactosidase activity, it can not decompose X-gal to exhibit leucoform. The leucoform colony was collected by using a loop, inoculated into LB medium 10 ml, and shake cultured at 37° C. for 16 hours, then plasmids were extracted from bacterial cells and purified by alkaline method. A part of the thus obtained recombinant plasmids was digested with the restriction enzyme BamHI to confirm obtainment of plasmid pUC 19::NEM-KS10, in which DNA fragment 3.0 kb was inserted into the pUC 19.

(2) Determination of a Terminal Sequence of BamHI DNA Fragment 3.0 kb Derived from *Streptomyces cyaneogriseus* subsp. *noncyanogenus* NRRL 15773

At first, a template DNA for the cycle sequencing was prepared. A primer set consisting of Expand Taq DNA polymerase buffer (Roche Inc., U.S.), dATP, dGTP, dCTP, dTTP, a synthetic DNA having base sequence of 5'-GTGCTG-CAAGGCGATTAAGTTGG-3' described in SEQ ID NO:1 and a synthetic DNA having base sequence of 5'-TCCG-GCTCGTATGTTGTGTGGA-3' described in SEQ ID NO:2 was added to the recombinant plasmid pUC19::NEM-KS10 obtained in example 1-(1), and Expand Taq DNA polymerase (Roche Inc. U.S.) was added thereto, then a reaction consisting of a cycle at 96° C. for 30 sec. and at 70° C. for 3 min. was repeated for 30 cycles. After completion of the reaction, exonuclease I (Amersham Pharmacia Biotech Inc., U.S.) and alkaline phosphatase (Amersham Pharmacia Biotech Inc., U.S.) were added thereto and reacted at 37° C. for 15 min., then treated at 80° C. for 10 min. for denaturing the enzymes. After denature of both enzymes, the cycle sequencing reaction was conducted DNA by adding IR labeled primer (Aloka Co. Ltd., Japan) and Thermo sequenase Fluorescent labeled primer cycle sequencing kit with 7-deaza-dGTP (Amersham Pharmacia Biotech Inc., U.S.) were added with using the template DNA of the above. After the reaction was completed, the reaction terminator was added and mixed to prepare the sample solution.

The sample solution was heated at 90° C. for 2 min. and ice-cooled, then the sequence electrophoresis was conducted. DNA sequencer Model 4000 Series (LI-COR Inc., U.S.) was used as an electrophoresis apparatus. Imaging analysis after the electrophoresis was performed by using Image Analysis Ver. 2.10 of Base Image IR Software Ver. 2.30. Based on the thus obtained each base sequence of DNA fragments, the amino acid sequences were detected by using BLAST. As a result, a sequence having high homology with *S. avermitilis* aveA4 in one end and a sequence having high homology with reductase of *S. avermitilis* in the other end were found. From these base sequences, a transcriptional direction of the nemadectin PKS gene of BamHI fragment was confirmed (refer to FIG. 1).

(3) Insertion of Viomycin Resistant Gene (Viomycin Phosphotransferase; vph) in NEM-KS10 Region A plasmid pUC19::NEM-KS10 was digested with a restriction enzyme BamHI, and the digested mixture was treated by agarose gel electrophoresis, then DNA fragment 3.0 kb containing KS10 region was isolated and purified. A DNA fragment, about 3.0 kb, 0.1 μg obtained by digesting pBluescript SK+ (TOYOBO CO. LTD., Japan) and BamHI digestion fragment 0.1 μg containing NEM-KS10 were mixed. The mixture was ligated with a reaction at 16° C. for 16 hours by using Ligation High (TOYOBO CO. LTD., Japan). The transformation was performed by contacting with the DNA ligation product 10 μl and the competent cell of *E. coli* DH5α to obtain the recombinant plasmid pBluescript SK+::NEM-KS10 which was the ligated plasmid with pBluescript SK+ and NEM-KS10 fragment. Further, the pBluescript SK+::NEM-KS10 was digested with the restriction enzymes HindIII (TAKARA BIO INC., Japan) and SstI (GIBCO BRL Inc., U.S.) and electrophoresed with agarose gel to obtain a DNA fragment containing NEM-KS10, about 3.0 kb. A plasmid pUC19 was digested with HindIII and SstI to obtain a DNA fragment, about 2.7 kb. Both DNA fragments, each 0.1 μg, were mixed and ligated with a reaction at 16° C. for 16 hours by using Ligation High. Using the DNA ligation product 10 μl, *E. coli* DH5α was transformed to obtain the plasmid pUC19-Bgl::NEM-KS10, which was the plasmid ligating NEM-KS10 fragment to pUC19-Bgl (inserting BglII cleavage sequence AGATCT into the outside of the both end EcoRI and HindIII of the multicloning site of pUC19).

Figure 2:
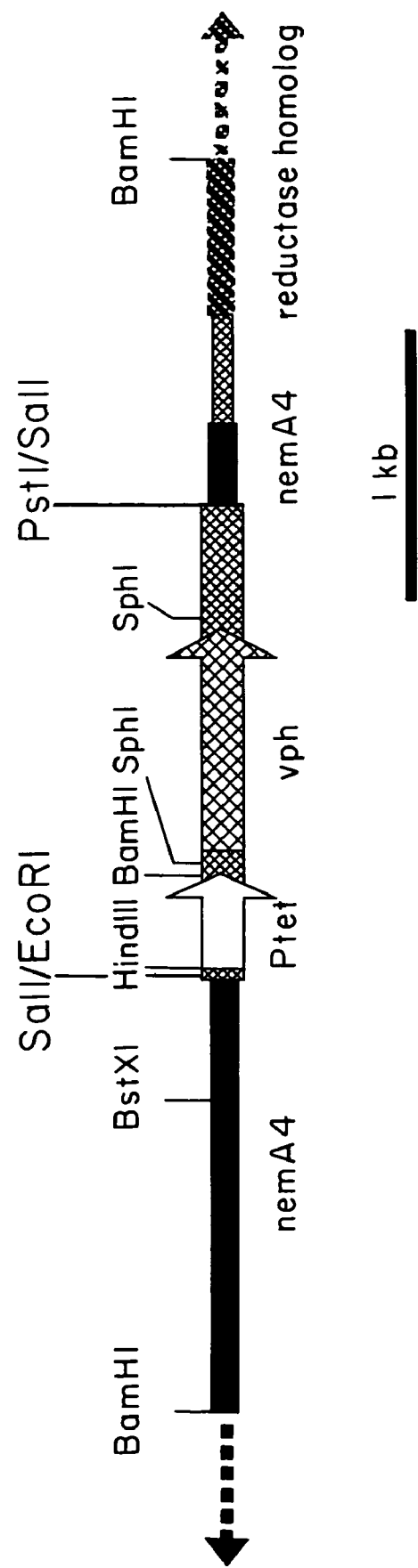
FIG. 2 is a restriction map of an insertion fragment of SalI region vph in nemadectin KS 10 region. Arrow indicates a direction for transcription.

A vph was obtained by digesting the plasmid pUC19::vph with a restriction enzymes EcoRI (TAKARA BIO INC., Japan) and PstI (TAKARA BIO INC., Japan), electrophoresing with agarose gel and isolating and purifying the DNA fragment, 1.7 kb, containing vph. A blunt end of EcoRI/PstI DNA fragment, 1.7 kb, containing vph was obtained by using BKL kit (TAKARA BIO INC., Japan) with a reaction at 37° C. for 15 min. After digesting the pUC19-Bgl::NEM-KS10 with the restriction enzyme SalI (TAKARA BIO INC., Japan), the blunt end of SalI cleavage site was prepared by using BKL kit. The fragments with blunt end and DNA fragment, 1.7 kb, with blunt end of the above were mixed, and ligation of DNA was performed by using Ligation High. *E. coli* DH5α was transformed by using the DNA ligation product 10 μl to obtain the recombinant plasmid pUC19-Bgl::NEM-KS10-vph, in which vph was inserted into the KS10 region (refer to FIG. 2). A selection of the transformant was performed by using LB medium containing ampicillin 50 μg/ml and tuberactinomycin N 150 μg/ml.

After digesting pUC19-Bgl::NEM-KS10-vph with the restriction enzyme BglII (TAKARA BIO INC., Japan), the product was electrophoresed with using agarose gel to isolate and purified the DNA fragment, 4.7 kb, containing KS10-vph region. After a vector plasmid pGM160 for *Streptomyces* was digested with the restriction enzyme BamHI, the product was electrophoresed with using agarose gel to isolate and purified the DNA fragment, 6.8 kb. Further, 5' terminal of DNA was dephosphorylated by using alkaline phosphatase (calf intestine). BamHI digested product of the pGM160 and DNA fraction, 4.7 kb, containing NEM-KS10-vph region, each 0.1 μg, were mixed to ligate DNA by using Ligation High. *E. coli* DH5α was transformed by using the DNA ligated product 10 μl to obtain the recombinant plasmid pGM160::NEM-KS10-vph. A selection of the transformant was performed by using LB medium containing ampicillin 50 μg/ml and tuberactinomycin N 150 μg/ml. Using the pGM160::NEM-KS10-vph, *E. coli* GM2929 hsdS::Tn10 was transformed. A selection of the transformant was performed by using LB medium containing chloramphenicol (Wako Pure Chemicals Inc., Japan) 30 μg/ml, ampicillin 50 μg/ml and tuberactinomycin N 150 μg/ml. A non-methylated plasmid DNA pGM160::NEM-KS10-vph was prepared from the transformant of *E. coli* GM2929 hsdS::Tn10.

(4) A Preparation of Protoplast from *Streptomyces cyaneogriseus* subsp. *noncyanogenus* NRRL 15773

Spore suspension 50 ml of lyophilized (at −30° C.) *Streptomyces cyaneogriseus* subsp. *noncyanogenus* was inoculated into YEME medium (in 500 ml Erlenmeyer flask) containing 30% w/v sucrose, 0.5% w/v glycine and 5 mM MgCl2, and cultured at 30° C. for 48 hours by rotary shaker. Bacterial cells were collected by centrifugation at 3000 rpm for 10 min. and the bacterial cells were washed with centrifugation for 10 min. A P10 medium containing egg lysozyme 1 mg/ml was added to the washed bacterial cells and suspended to form protoplasts at 30° C. for 30 minutes. After well mixing with adding P10 medium 10 ml, the protoplasts suspension was filtered through a cotton plug filter to remove lysozyme indigested mycelia. The protoplast suspension passed through the cotton plug filter was centrifuged at 3000 rpm for 10 min. to precipitate the protoplasts. Supernatant was removed and the precipitate was well suspended with P10 medium 10 ml, and the suspension was centrifuged at 3000 rpm for 10 min. to precipitate the protoplasts. The P10 medium 10 ml was added again to the precipitate to suspend the protoplasts, and the protoplasts were washed by centrifugation. The thus obtained washed protoplasts were suspended in the P10 medium 5 ml. The suspension, each 0.1 ml, was dispensed into Eppendorf tube and stored at −80° C.

(5) Preparation of Gene Recombinant to which Viomycin Resistant Gene (Viomycin Phosphotransferase; vph) is Introduced in KS10 Region of Nemadectin PKS on the Chromosome The recombinant plasmid pGM160::NEM-KS10-vph, about 1 μg, obtained in example 1-(3) and protoplasts, about $5\times10^8$, of *Streptomyces cyaneogriseus* subsp. *noncyanogenus* obtained in example 1-(4) were poured in a sterilized Eppendorf tube, and immediately added and mixed with 25% polyethylene glycol MW1000 solution (2.5% sucrose, 0.05% $KH_2PO_4$, 0.1 M $CaCl_2$ and 50 mM Tris-maleate, pH 8.0) and allowed to stand at room temperature for 1 min. After P10 medium 450 μl was added and mixed well, each 100 μl thereof was placed on R2YE agar medium and was spread over together with soft agar medium 2.5 ml. After incubating at 30° C. for 20 hours, a soft agar medium 2.5 ml containing thiostrepton (Sigma-Aldrich Co., U.S.) 200 μg/ml was overlaid. The medium was cultured at 30° C. for and the transformant resistant to thiostrepton was-obtained.

The transformant resistant to thiostrepton grown on the surface of R2YE agar medium was scratched aseptically. Mycelia were cut by using homogenizer and the cleaved mycelia were spread over on YMS agar medium. The medium was cultured at 37° C. for 4 days, and sporogenous mycelia were replicated on the YMS agar medium containing tuberactinomycin N as a master plate. The plate was cultured at 30° C. for 2 days, and tuberactinomycin resistant colonies were selected, then each colony was spread over on YMS agar medium. The medium was cultured at 30° C. for 5 days, and sporogenous mycelia were replicated on the YMS agar medium containing thiostrepton 20μg/ml as a master plate, then the plate was cultured at 30° C. for 2 days. Strains resistant to tuberactinomycin and sensitive to thiostrepton were selected and confirmed the insertion of the vph in the KS10 region of nemadectin PKS on the chromosome by means of Southern hybridization as well as confirming no production of nemadectin. The thus obtained each strain was referred to *Streptomyces cyaneogriseus* subsp. *noncyanogenus* ΔnemA4::vph.

The present strain *Streptomyces cyaneogriseus* subsp. *noncyanogenus* ΔnemA4::vph was deposited in the International Patent Organism Depositary, National Institute of Advanced Industrial Science and Technology, AIST Tsukuba Central 6, 1-1, Higashi 1-chome, Tsukuba-shi, Ibaraki-ken, 305-8566 Japan based on Budapest Treaty on the International Recognition of the Deposit of Microorganisms for the Purposes of Patent Procedure as accession number FERM BP-8393 on Jun. 6, 2003.

(6) Obtaining Avermectin Synthetase Gene aveA3 Derived from *Streptomyces avermitilis*

A chromosomal DNA of *Streptomyces avermitilis* was digested with the restriction enzyme EcoRI and electrophoresed with low melting point agarose gel. A DNA fragment, 39912 bp, described in SEQ ID NO:3 containing total aveA3-4 was cut out with gel. The gel was isolated and purified by means of phenol extraction, phenol-chloroform extraction and alcohol precipitation. In addition, a chromosome inserted vector plasmid pTG1int-cos was digested with the restriction enzyme EcoRI and electrophoresed with agarose gel to isolate and purify DNA fragment, 5.2 kb. The EcoRI digested pTG1ing-cos was dephosphorylated at 5' terminal of the DNA by using alkaline phosphatase (calf intestine), and about 0.5 μg thereof was mixed with the DNA fragment, 39912 bp, about 2 μg, containing the total aveA3-4, and was ligated with the reaction at 25° C. for 10 min. by using Ligation kit ver. 2 (TAKARA BIO INC., Japan) solution I and solution II.

After the DNA ligate was treated with alcohol precipitation, the DNA was dissolved in TE buffer 2 μl. The solution was added to Packaging Extract of ReadyToGo Lambda Packaging Kit (Amersham-Pharmacia Biotech, Inc., U.S.), and added sterilized water 23 μl, then allowed to stand at room temperature for 2 hours. A phage diluted buffer (SM buffer) 0.5 ml and chloroform 30 μl were added thereto and mixed by gentle tumbling. The mixture was centrifuged at 13200 rpm for 30 sec. and the supernatant was transferred to a new sterilized Eppendorf tube to obtain λ phage packaging solution.

(7) Obtaining *E. coli* BL21 recA Deficient Strain Maintaining Avermectin Aglycon Synthetase Gene aveA3-4

Using the λ phage packaging solution obtained in example 1-(6), a transduction was performed with the host cell *E. coli* BL21 recA deficient strain. The host cell *E. coli* BL21 recA deficient strain was shake cultured with LB medium at 37° C. for overnight, and was added to LB medium added with 0.4% maltose to become 1% and cultured 37° C. for 3 hours. Cells were collected by centrifugation and were washed with using 10 mM magnesium sulfate solution. Bacterial cells were further collected by centrifugation and were suspended in adequate amount of 10 mM magnesium sulfate solution to obtain the host bacterial cell solution. The host bacterial cell solution and the λ phage packaging solution obtained in example 1-(6) were mixed at a rate 1:1 in an Eppendorf tube, then allowed to stand at room temperature for 30 minutes. Thereafter, LB medium was added and shaken at 30° C. for 1.5 hour, then the cultured medium was spread on the LA medium containing kanamycin (50 μg/ml) and cultured at 30° C. for overnight. Colonies resistant to kanamycin were cultured in 96 well test plate as a library, and clones maintaining cosmid DNA hybridized with the synthetic DNA described in SEQ ID NO:4 were selected. The recombinant DNA maintaining avermectin aglycon synthetase gene aveA3-4 was purified from the bacterial cells which were cultured for overnight by using LB medium containing kanamycin (50 μg/ml) according to the conventional alkaline method.

EXAMPLE 2

Introduction of Avermectin Biosynthesis Genes aveA3-4 into Nemadectin PKS Module 10vph The spore suspension of nemadectin PKS module 10vph insertion strain obtained in example 1-(5) was inoculated into YEME medium (500 ml Erlenmeyer flask) containing 50 ml of 30% w/v sucrose, 0.5% w/v glycine and 5mM $MgCl_2$, and cultured at 30° C. for 48 hours in the rotary shaker. Mycelia were collected by centrifugation at 3000 rpm for 10 min. After P10 medium 20 ml was added and suspended well, the suspension was centrifuged at 3000 rpm for 10 min. to wash mycelia. The P10 medium containing egg lysozyme 1 mg/ml was added to the washed mycelia to suspend and to generate the protoplast by keeping at 30° C. for 30 minutes. After well mixing with adding P10 medium 10 ml, the protoplast suspension was passed through a cotton plug filter to remove lysozyme indigested mycelia. The protoplast suspension which was passed through the cotton plug filter was centrifuged at 3000 rpm for 10 min. to precipitate the protoplast. After removing the supernatant and suspending well with P10 medium 10 ml, the protoplast was precipitated by centrifuging at 3000 rpm for 10 min. The P10 medium 10 ml was again added thereto and the protoplast was suspended and washed by centrifugation. The obtained washed protoplast was suspended in P10 medium 5 ml. The suspension, each 0.1 ml, was dispensed in the sterilized Eppendorf tube and stored at −80° C.

The pTG1int-cos::aveA3-4, about 1 μg, prepared in example 1-(7) was added to the protoplast hereinabove and immediately added and mixed with 25% polyethylene glycol MW1000 solution (2.5% sucrose, 0.05% $KH_2PO_4$, 0.1 M $CaCl_2$ and 50 mM Tris-maleate, pH 8.0) 500 μl and allowed to stand at room temperature for 1 min. After P10 medium 450 μl was added and mixed well, each 100 μl thereof was placed on R2YE agar medium and was spread over together with soft agar medium 2.5 ml. After incubating at 30° C. for 20 hours, a soft agar medium 2.5 ml containing neomycin (Sigma-Aldrich Co., U.S.) 100 μp/ml was overlaid. The medium was cultured at 30° C. for 5 days to obtain the transformant resistant to neomycin. The transformant resistant to neomycin grown on the surface of R2YE agar medium was spread aseptically over the YMS agar medium containing neomycin 2 μp/ml. The thus obtained each strain was referred to *Streptomyces cyaneogriseus* subsp. *noncyanogenus* ΔnemA4::vph $attB_{TG1}$::aveA4-aveA3-aveE.

EXAMPLE 3

Introduction of aveR to *Streptomyces cyaneogriseus* subsp. *noncyanogenus* ΔnemA4::vph $attB_{TG1}$::aveA4-aveA3-aveE The vector plasmid pUCBM21::aveR ligated with the restriction enzyme AgeI DNA fragment containing the transcriptional regulatory gene aveR of avermectin biosynthesis genes described in SEQ ID NO:5 was digested with restriction enzymes XbaI and HindIII, and electrophoresed with agarose gel to isolate and purify DNA fragment, 3.27 kb, containing aveR. The XbaI-HindIII fragment, 3.27 kb, containing aveR was ligated into XbaI and HindIII recognition sites of the chromosomal integrative vector plasmid pUC19aad3"-intΦC31 to transform *E. coli* BL21ΔrecA.

The spore suspension of *Streptomyces cyaneogriseus* subsp. *noncyanogenus* ΔnemA4::vph $attB_{TG1}$::aveA4-aveA3-aveE obtained in example 2 was inoculated into YEME medium (500 ml Erlenmeyer flask) containing 50 ml of 30% w/v sucrose, 0.5% w/v glycine and 5 mM $MgCl_2$, and cultured at 30° C. for 48 hours in the rotary shaker. Mycelia were collected by centrifugation at 3000 rpm for 10 min. After P10 medium 20 ml was added and suspended well, the suspension was centrifuged at 3000 rpm for 10 min. to wash mycelia. The P10 medium containing egg lysozyme 1 mg/ml was added to the washed mycelia to suspend and to generate the protoplast by keeping at 30° C. for 30 minutes. After well mixing with adding P10 medium 10 ml, the protoplast suspension was passed through a cotton plug filter to remove lysozyme indigested mycelia. The protoplast suspension which was passed through the cotton plug filter was centrifuged at 3000 rpm for 10 min. to precipitate the protoplast. After removing the supernatant and suspending well with P10 medium 10 ml, the protoplast was precipitated by centrifuging at 3000 rpm for 10 min. The P10 medium 10 ml was again added thereto and the protoplast was suspended and washed by centrifugation. The obtained washed protoplast was suspended in P10 medium 5 ml. The suspension, each 0.1 ml, was dispensed in the sterilized Eppendorf tube and stored at −80° C. The plasmid DNA pUC19aad3"-intΦC31::aveR, about 1 μg, obtained hereinabove was added to the protoplast hereinabove and immediately added and mixed with 25% polyethylene glycol MW1000 solution (2.5% sucrose, 0.05% $KH_2PO_4$, 0.1 M $CaCl_2$ and 50 mM Tris-maleate, pH 8.0) 500 μl and allowed to stand at room temperature for 1 min.

After P10 medium 450 μl was added and mixed well, each 100 μl thereof was placed on R2YE agar medium and was spread over together with soft agar medium 2.5 ml. After incubating at 30° C. for 20 hours, a soft agar medium 2.5 ml containing spectinomycin 3 mg/ml was overlaid. The medium was cultured at 30° C. for 5 days to obtain the transformant resistant to spectinomycin. The transformant resistant to spectinomycin grown on the surface of R2YE agar medium was spread aseptically over the YMS agar medium containing spectinomycin 300 μp/ml. The thus obtained each strain was referred to *Streptomyces cyaneogriseus* subsp. *noncyanogenus* ΔnemA4::vph $attB_{TG1}$::aveA4-aveA3-aveE $attB\phi_{C31}$::aveR.

EXAMPLE 4

Culturing *Streptomyces cyaneogriseus* subsp. *noncyanogenus* ΔnemA4::vph $attB_{TG1}$::aveA4-aveA3-aveE $attB\phi_{C31}$::aveR and isolation and purification of the product The strain integrated with aveA3-4 and aveR in the strain inserted with vph of nemadectin PKS module 7 on the chromosome obtained in example 3 was inoculated in a nemadectin seed culture medium and cultured at 30° C. for 3 days. The cultured medium 1 ml was added to the nemadectin production medium 50 ml dispensed in the 500 ml Erlenmeyer flask. This was shake cultured at 28° C. for 5 days under 180 rpm and centrifuged at 3000 rpm for 10 min. to obtain mycelia. The obtained mycelia were suspended with acetone, stirred at room temperature for 1 hour and the mycelia and acetone layer were collected separately. The solvent was distilled from the acetone layer. Water and chloroform were added to the substance dried by distillation of the solvent and the mixture was stirred. Chloroform layer was collected separately and sodium sulfate anhydride was added for dehydration. Solvent was distilled off from the chloroform layer. The resultant crude extract was dissolved in small amount of chloroform. The solution was charged on a column of silica gel(Sigma-Aldrich Co., U.S.) equilibrated with chloroform. After washing the column with chloroform, the column was washed with 25% v/v ethyl acetate/chloroform to remove fractions without containing C-13 hydroxyl nemadectin. Subsequently, fractions eluted with 40% v/v ethyl acetate/chloroform were removed and fractions containing large amount of C-13 hydroxyl nemadectin eluted with 50% v/v ethyl acetate/chloroform were collected. The obtained eluate was dried in vacuo to obtain yellowish oily substance. The thus obtained yellowish oily substance was isolated and purified by the following condition using HPLC.

Figure 3:
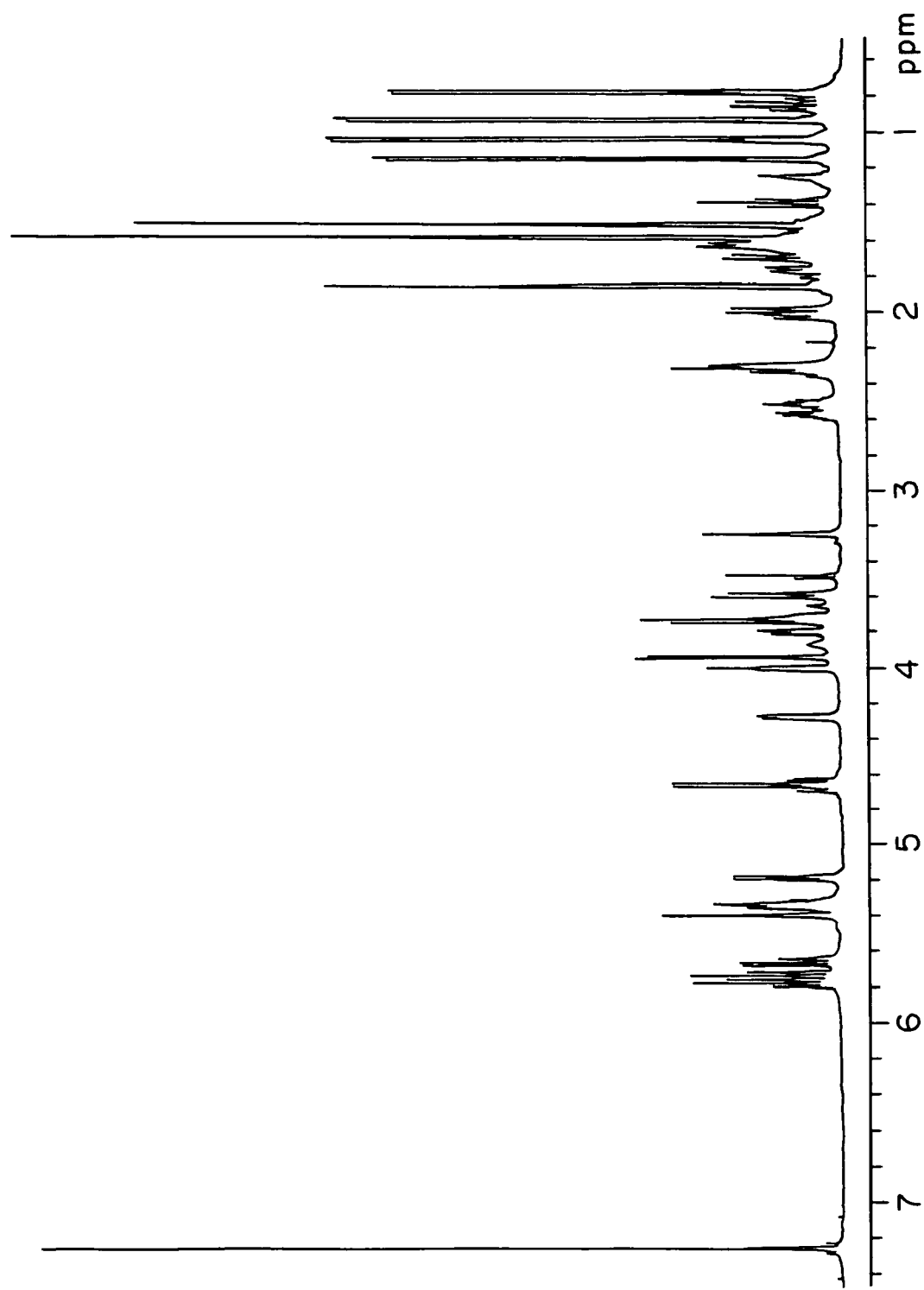
FIG. 3 is $^1$H-NMR spectrum of C-13 hydroxylnemadectin.
Figure 4:
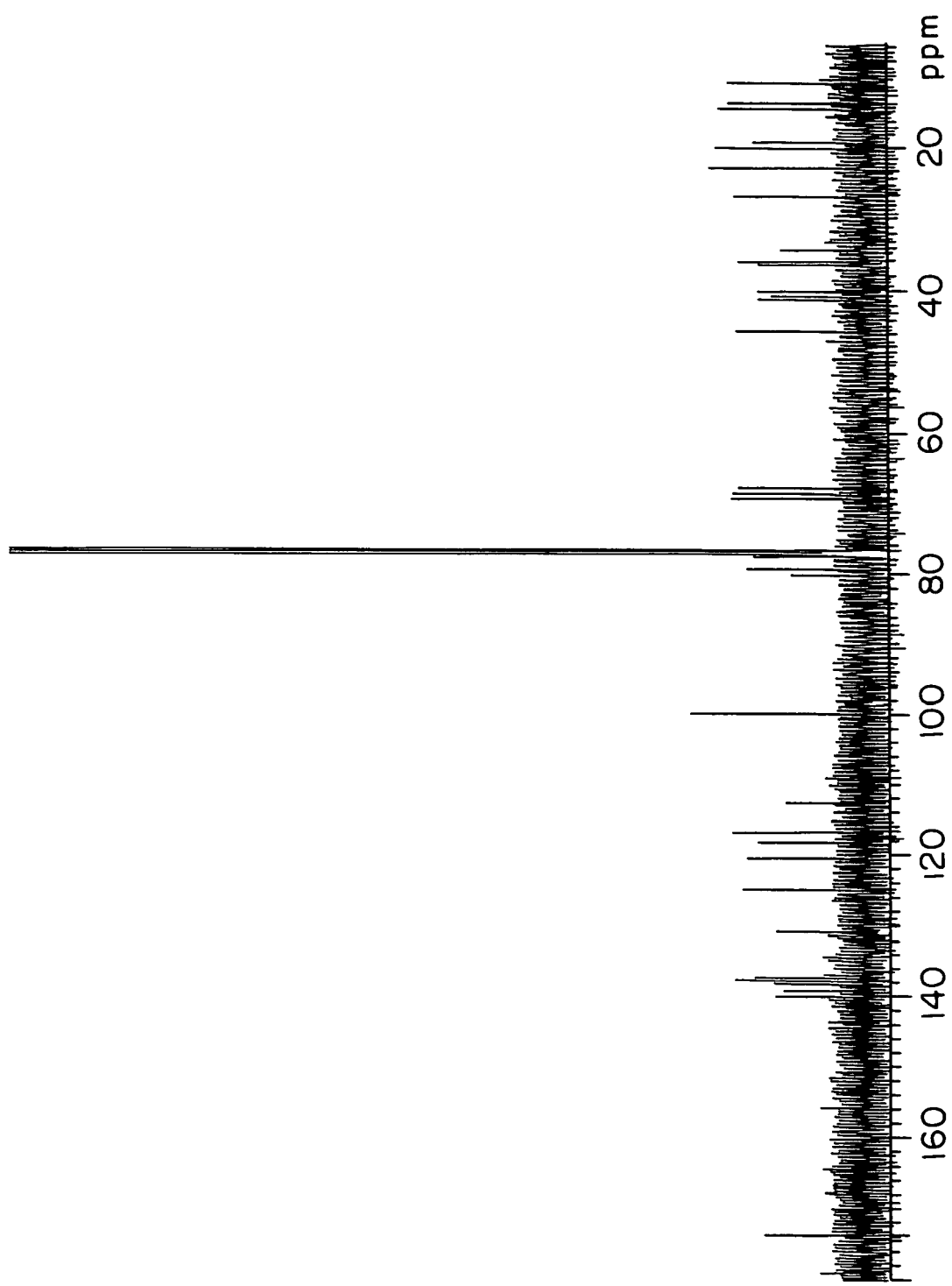
FIG. 4 is $^{13}$H-NMR spectrum of C-13 hydroxylnemadectin.
Figure 5:
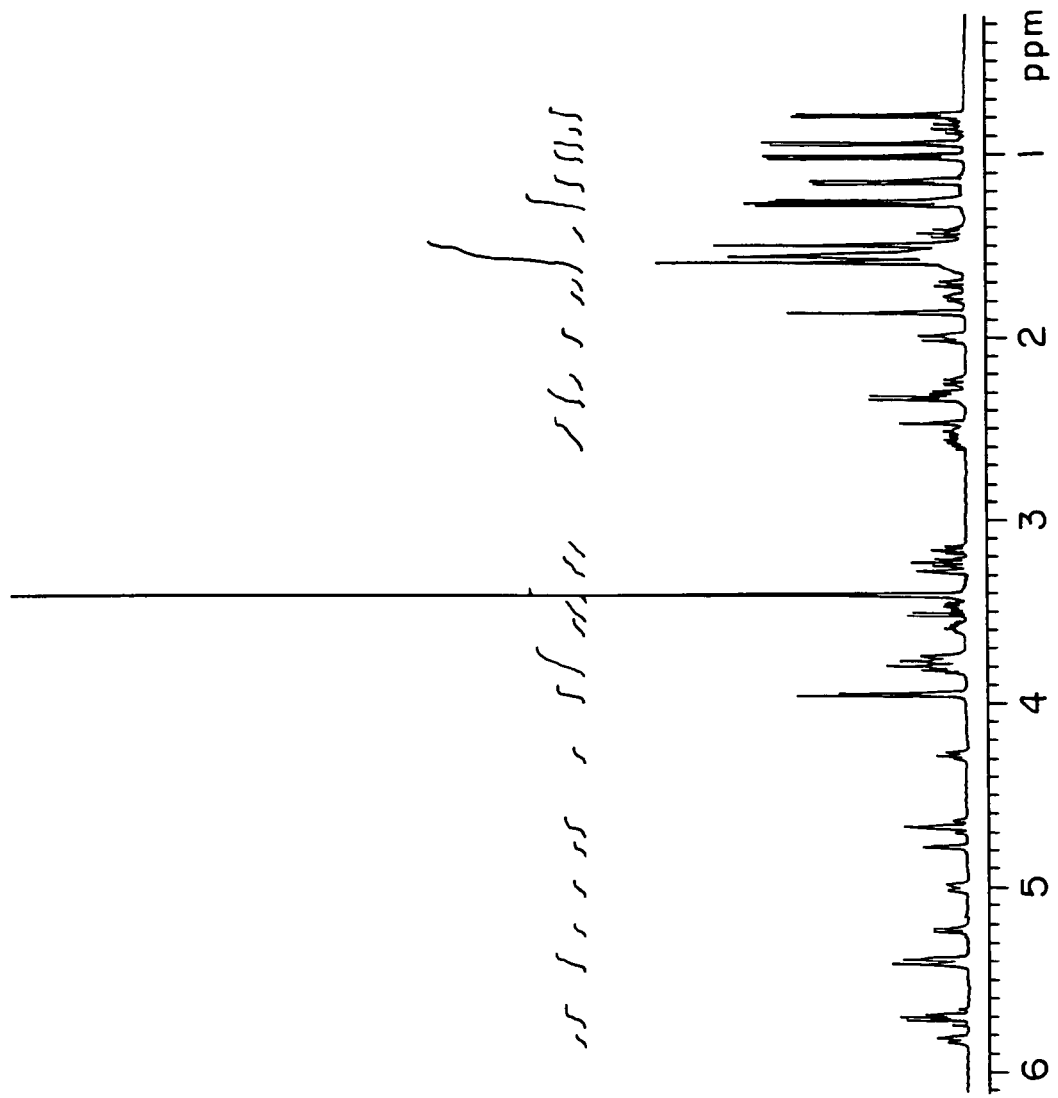
FIG. 5 is $^1$H-NMR spectrum of C-13 glycosylnemadectin.
Figure 6:
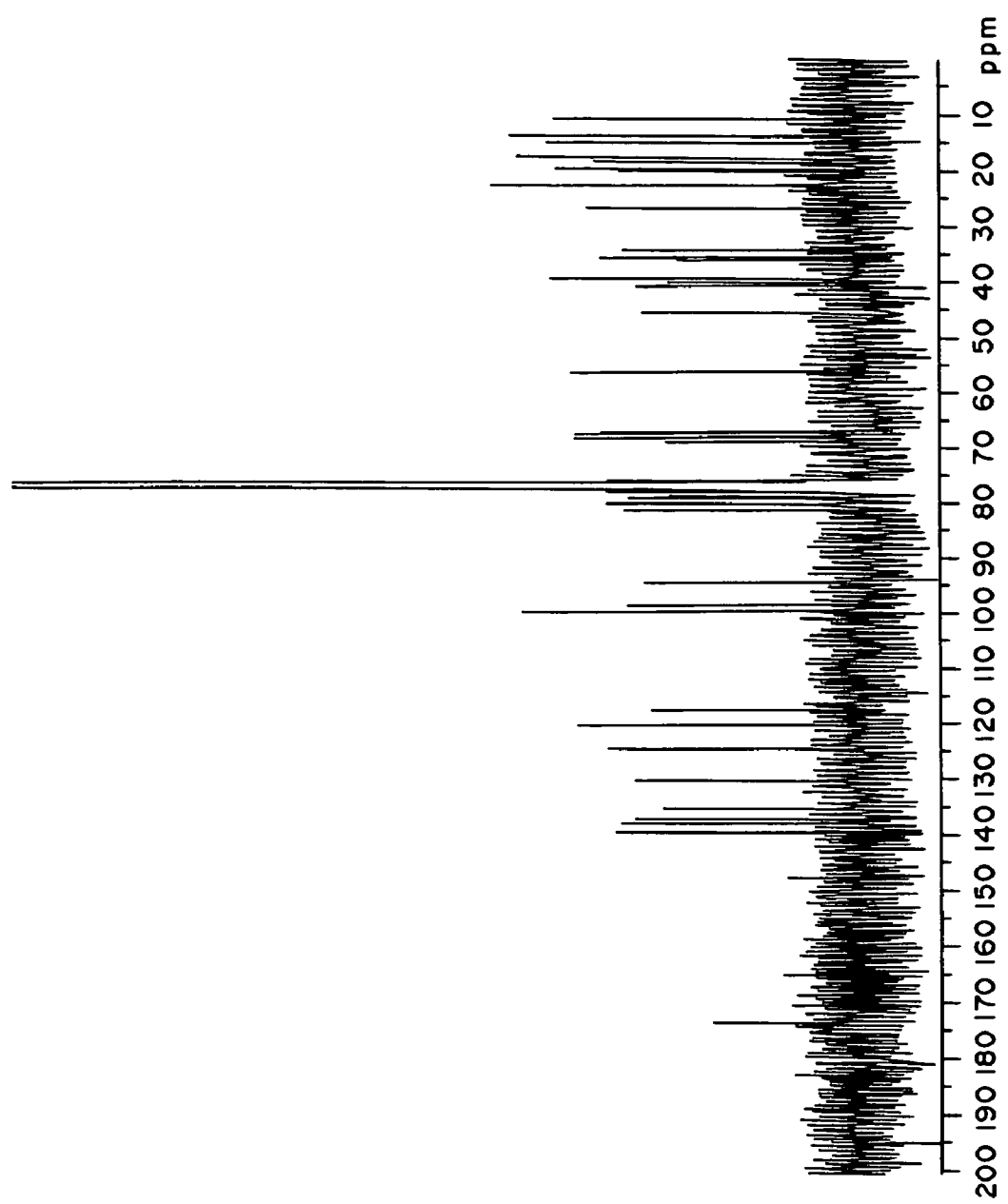
FIG. 6 is $^{13}$H-NMR spectrum of C-13 glycosylnemadectin.

When Pegasil ODS column (ODS: 3 µm; column size: 20 φ mm×250 mm; Senshu Scientific Co., Ltd., Japan). was used under the condition of the mobile phase of a mixed solvent consisting of acetonitrile 50%, methanol 18% and water 32%, detection at 246 nm and separation at flow rate 8 ml/min., a component with the retention time 28 minutes was isolated. The obtained compound was analyzed the structure by $^1$H-NMR spectrum (refer to FIG. 3) data, $^{13}$C-NMR spectrum (refer to FIG. 4) data and mass spectrum data (M+1=629), and was confirmed to be C-13 hydroxyl nemadectin α (molecular formula: $C_{36}H_{52}O_9$) represented by the following formula.

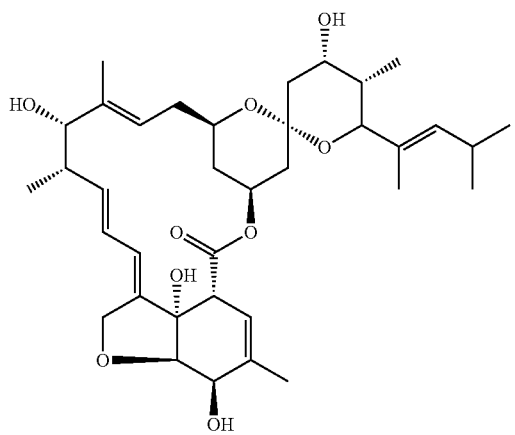

EXAMPLE 5

Obtaining avermectin glycosylation genes aveBI-BVIII derived from *Streptomyces avermitilis*

A DNA fragment, 11041 bp, described in SEQ ID NO:6, i.e. pUC19::aveBI-BVIII ligated with DNA containing total aveBI-BVIII, was digested with restriction enzymes XbaI and HindIII, and the DNA fragment containing total aveBI-BVIII was electrophoresed with low melting point agarose gel.

The gel was isolated and purified by means of phenol extraction, phenol-chloroform extraction and alcohol precipitation. In addition, a chromosome inserted vector plasmid pUC19intR4-tsr was digested with the restriction enzyme XbaI-HindIII and electrophoresed with agarose gel to isolate and purify DNA fragment, 11 kb. DNA fragments were ligated by using Ligation High, and *E. coli* BL21ΔrecA was transformed with using the DNA ligation product 10 µl to obtain the recombinant plasmid pUC19intR4-tsr::aveBI-BVIII. A selection of the transformant was performed by using LB medium containing ampicillin 50 µg/ml.

EXAMPLE 6

Introduction of avermectin glycosylation and oleandrose biosynthesis genes aveBI-BVIII derived from *Streptomyces avermitilis* into *Streptomyces cyaneogriseus* subsp. *noncyanogenus* ΔnemA4::vph attB$_{TGi}$::aveA4-aveA3-aveE attBφ$_{C31}$::aver Spore suspension of *Streptomyces cyaneogriseus* subsp. *noncyanogenus* ΔnemA4::vph attB$_{TG1}$::aveA4-aveA3-aveE attBφ$_{C31}$::aveR obtained in example 3 was inoculated into YEME medium (500 ml Erlenmeyer flask) containing 50 ml of 30% w/v sucrose, 0.5% w/v glycine and 5 mM MgCl$_2$, and cultured at 30° C. for 48 hours in the rotary shaker. Mycelia were collected by centrifugation at 3000 rpm for 10 min. After P10 medium 20 ml was added and suspended well, the suspension was centrifuged at 3000 rpm for 10 min. to wash mycelia. The P10 medium containing egg lysozyme 1 mg/ml was added to the washed mycelia to suspend and to generate the protoplast by keeping at 30° C. for 30 minutes. After well mixing with adding P10 medium 10 ml, the protoplast suspension was passed through a cotton plug filter to remove lysozyme indigested mycelia. The protoplast suspension which was passed through the cotton plug filter was centrifuged at 3000 rpm for 10 min. to precipitate the protoplast. After removing the supernatant and suspending well with P10 medium 10 ml, the protoplast was precipitated by centrifuging at 3000 rpm for 10 min. The P10 medium 10 ml was again added thereto and the protoplast was suspended and washed by centrifugation. The obtained washed protoplast was suspended in P10 medium 5 ml. The suspension, each 0.1 ml, was dispensed in the sterilized Eppendorf tube and stored at −80° C. The plasmid DNA pUC19intR4-tsr::aveBI-BVIII, about 1 pg, obtained in example 5 was added to the protoplast hereinabove and immediately added and mixed with 25% polyethylene glycol MW1000 solution (2.5% sucrose, 0.05% KH$_2$PO$_4$, 0.1 M CaCl$_2$ and 50 mM Tris-maleate, pH 8.0) 500 µl and allowed to stand at room temperature for 1 min.

After P10 medium 450 µl was added and mixed well, each 100 µl thereof was placed on R2YE agar medium and was spread over together with soft agar medium 2.5 ml. After incubating at 30° C. for 20 hours, a soft agar medium 2.5 ml containing thiostrepton 200 µp/ml was overlaid. The medium was cultured at 30° C. for 5 days to obtain the transformant resistant to thiostrepton. The transformant resistant to thiostrepton grown on the surface of R2YE agar medium was spread aseptically over the YMS agar medium containing thiostrepton 20 µg/ml. The thus obtained each strain was referred to *Streptomyces cyaneogriseus* subsp. *noncyanogenus* ΔnemA4::vph attB$_{TG1}$::aveA4-aveA3-aveE attBφ$_{C31}$::aveR attB$_{R4}$::aveBI-BVIII.

EXAMPLE 7

Culturing *Streptomyces cyaneogriseus* subsp. *noncyanogenus* ΔnemA4::vph attB$_{TG1}$::aveA4-aveA3-aveE attBφ$_{C31}$::aveR attB$_{R4}$::aveBI-BVIII and Isolation and Purification of Product The strain integrated with aveA3-4, aveR and aveBI-BVIII in the strain inserted with vph of nemadectin PKS module 10 on the chromosome obtained in example 6 was inoculated in a nemadectin seed culture medium and cultured at 30° C. for 3 days. The cultured medium 1 ml was added to the nemadectin production medium 50 ml dispensed in the 500 ml Erlenmeyer flask. This was shake cultured at 28° C. for 5 days under 180 rpm and centrifuged at 3000 rpm for 10 min. to obtain mycelia. The obtained mycelia were suspended with acetone, stirred at room temperature for 1 hour and the mycelia and acetone layer were collected separately. The solvent was distilled from the acetone layer. Water and chloroform were added to the substance dried by distillation of the solvent and the mixture was stirred. Chloroform layer was collected separately and sodium sulfate anhydride was added for dehydration. Solvent was distilled off from the chloroform layer. The resultant crude extract was dissolved in small amount of chloroform. The solution was charged on a column of silica gel (Sigma-Aldrich Co., U.S.) equilibrated with chloroform. After washing the column with chloroform, the column was washed with 30% v/v ethyl acetate/chloroform to remove fractions without containing C-13 glycosylnemadectin. Subsequently, fractions eluted with 40% v/v ethyl acetate/chloroform and 50% v/v ethyl acetate/chloroform were collected. Each obtained eluate was dried in vacuo to obtain yellowish oily substance. The thus obtained yellowish oily substance was isolated and purified by the following condition using HPLC.

Pegasil ODS column (3 μm; column size: 20ϕmm×250 mm; Senshu Scientific Co., Ltd., Japan) was used and a solvent mixture in a ratio of acetonitrile:methanol:water=55:18:27 was used as the mobile phase. A flow rate was set at 6 ml/min., and a component having the retention time 120 minutes was collected with the indication of absorption at 246 nm. The obtained compound was analyzed the structure by $^1$H-NMR spectrum (refer to FIG. 5) data, $^{13}$C-NMR spectrum (refer to FIG. 6) data and mass spectrum data (M+1=917), and was confirmed to be C-13 glycosylnemadectin a (molecular formula: $C_{50}H_{76}O_{15}$) represented by the following formula.

Solution for terminating cycle sequencing reaction

| | |
|---|---|
| Bromophenol Blue | 0.02% |
| EDTA (pH 8.0) | 20 mM |
| Formamide | 95% |

YEME medium

| | |
|---|---|
| Yeast extract (Difco Laboratories) | 3 g |
| Malt extract (Oxoid Ltd.) | 3 g |
| Peptone (Difco Laboratories) | 5 g |
| Glucose | 10 g |
| Sucrose | 300 g |
| Distilled water | 1000 ml | pH not adjusted, 121° C., high pressure steam sterilization for 1 min.

Trace element solution

| | |
|---|---|
| Ferric chloride 6 hydrate | 200 mg |
| Zinc chloride | 40 mg |
| Cupric chloride 2 hydrate | 10 mg |
| Manganese chloride 4 hydrate | 10 mg |
| Sodium borate 10 hydrate | 10 mg |
| Ammonium molybdate 4 hydrate | 10 mg |
| Distilled water | 1000 ml |

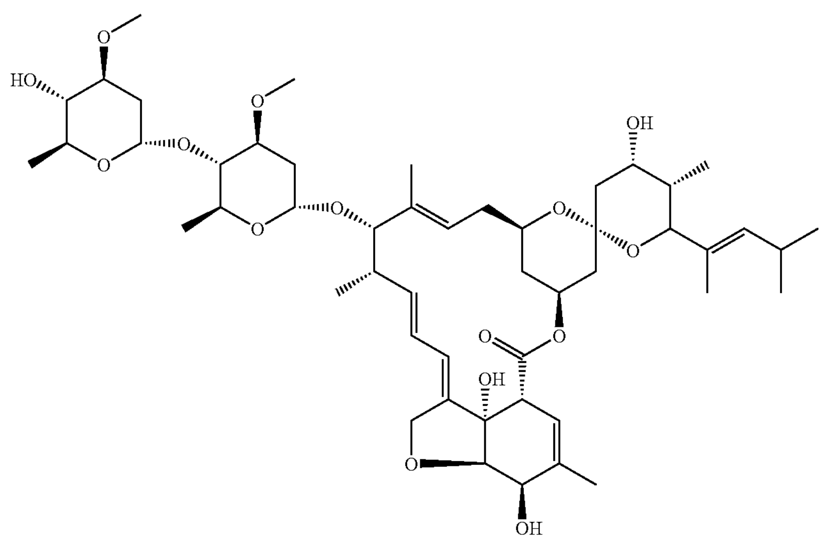

Compositions of various media and buffer used in examples hereinabove are shown as follows.

Buffer for dilution of phage (SM buffer)

| | |
|---|---|
| Tris-HCl (ph 7.5) | 10 mM |
| Sodium chloride | 100 mM |
| Magnesium sulfate 7$H_2O$ | 10 mM |

P10 medium

| | |
|---|---|
| Sucrose | 103 g |
| Potassium sulfate | 0.25 g |
| Magnesium chloride 6 hydrate | 2.03 g |
| Trace elements solution | 2.0 ml |

After high pressure steam sterilization at 121° C. for 15 min., following components are aseptically added.

| | |
|---|---|
| 0.5% potassium phosphate | 10 ml |
| 3.68% potassium chloride 2 hydrate | 100 ml |
| 0.25 M TES* (pH 7.2) | 100 ml |

*N-tris(hydroxymethyl)methyl-2-aminoethanesulfonate

R2YE agar medium

| | |
|---|---|
| Sucrose | 103 g |
| Potassium sulfate | 0.25 g |
| Magnesium chloride 6 hydrate | 10.12 g |
| Glucose | 10 g |
| Casamino acid (Difco Laboratories) | 0.1 g |
| Agar | 22 g |
| Distilled water | 800 ml |

After high pressure steam sterilization at 121° C. for 15 min., following components are aseptically added.

| | |
|---|---|
| Trace elements solution | 2 ml |
| 0.5% potassium phosphate | 10 ml |
| 3.68% potassium chloride 2 hydrate | 80 ml |
| 20% L-proline | 15 ml |
| 0.25 M TES (pH 7.2) | 100 ml |
| 10% yeast extract (Difco Laboratories) | 50 ml |
| 1 M sodium hydroxide | 5 ml |

Soft agar medium

| | |
|---|---|
| Sucrose | 103 g |
| Magnesium chloride 6 hydrate | 10.12 g |
| Agar (Difco Laboratories) | 6.5 g |
| Distilled water | 820 ml |

After high pressure steam sterilization at 121° C. for 15 min., following components are aseptically added.

| | |
|---|---|
| 3.68% potassium chloride 2 hydrate | 80 ml |
| 0.25 M TES (pH 7.2) | 100 ml |

YMS agar medium

| | |
|---|---|
| Malt extract (Difco Laboratories) | 10 g |
| Yeast extract (Difco Laboratories) | 4 g |
| Soluble starch (Difco Laboratories) | 4 g |
| Agar | 20 g |
| Distilled water | 1000 ml |

After adjusting pH 7.4 by adding 2M potassium hydroxide, subjecting to high pressure steam sterilization at 121° C. for 15 min. After the sterilization, magnesium chloride and potassium nitrate were added to be 10 mM and 8 mM, respectively.

LA medium

| | |
|---|---|
| Tryptone (Oxoid Ltd.) | 10 g |
| Yeast extract (Oxoid Ltd.) | 5 g |
| Sodium chloride | 5 g |
| Agar | 15 g |
| Distilled water | 1000 ml |

After adjusting pH 7.2 by adding 2M potassium hydroxide, subjecting to high pressure steam sterilization at 121° C. for 15 min.

Seed culture medium for nemadectin producing strain

| | |
|---|---|
| Glucose | 10 g |
| Dextrin | 20 g |
| Yeast extract | 5 g |
| NZ-amine A | 5 g |
| Calcium carbonate | 1 g |
| Distilled water | 1000 ml | pH not adjusted. High pressure steam sterilization at 121° C. for 15 min.

Culture medium for nemadectin production

| | |
|---|---|
| Glucose | 50 g |
| Cotton seed powder | 25 g |
| Calcium carbonate | 7 g |
| Distilled water | 1000 ml | pH not adjusted. High pressure steam sterilization at 121° C. for 15 min.

INDUSTRIAL APPLICABILITY

As described hereinabove, the present invention relates to the invention comprising introducing DNA of the nemadectin analogous compound producing microorganism into the nemadectin producing microorganism belonging to genus *Streptomyces*, producing and accumulating C-13 hydroxyl nemadectin and C-13 glycosylnemadectin, and collecting the same. The stereoselectively glycosylated nemadectin derivatives can be effectively obtained by preparing C-13 glycosylnemadectin by means of molecular genetic technology. Improvements in biological activities such as anti-insects and anti-parasites can be expected.

What is claimed is:

1. An isolated microorganism strain belonging to *Streptomyces cyaneogriseus* subspecies *noncyanogenus* and having ability to produce C-13 glycosidated nemadectin, wherein said microorganism strain is *Streptomyces cyaneogriseus* subsp. *noncyanogenus* ΔnemA4::vph attB$_{TG1}$::aveA4-aveA3-aveE attBφ$_{c31}$: :aveR attBR$_{R4}$::aveBI-BVIII (FERM BP-8394).

\* \* \* \* \*